United States Patent
Paquette et al.

(10) Patent No.: US 9,863,007 B2
(45) Date of Patent: *Jan. 9, 2018

(54) DETECTION OF TOXIGENIC STRAINS OF CLOSTRIDIUM DIFFICILE

(71) Applicant: Geneohm Sciences Canada, Inc., Quebec City (CA)

(72) Inventors: Nancy Paquette, Quebec (CA); Marie-Eve Rochette, Quebec (CA); Rachel Labourdette, Quebec (CA)

(73) Assignee: Geneohm Sciences Canada, Inc., Quebec (CA)

( * ) Notice: Subject to any disclaimer, the term of this patent is extended or adjusted under 35 U.S.C. 154(b) by 133 days.

This patent is subject to a terminal disclaimer.

(21) Appl. No.: 14/752,586

(22) Filed: Jun. 26, 2015

(65) Prior Publication Data

US 2015/0292004 A1 Oct. 15, 2015

Related U.S. Application Data

(63) Continuation of application No. 12/203,694, filed on Sep. 3, 2008, now Pat. No. 9,096,638.

(60) Provisional application No. 60/970,492, filed on Sep. 6, 2007.

(51) Int. Cl.
| | | |
|---|---|---|
| *C12Q 1/68* | (2006.01) | |
| *C07H 21/00* | (2006.01) | |
| *C07H 21/04* | (2006.01) | |

(52) U.S. Cl.
CPC ............. *C12Q 1/689* (2013.01); *C07H 21/00* (2013.01); *C07H 21/04* (2013.01); *C12Q 2561/101* (2013.01); *C12Q 2561/113* (2013.01)

(58) Field of Classification Search
CPC ................................................... C12Q 1/689
See application file for complete search history.

(56) References Cited

U.S. PATENT DOCUMENTS

| | | |
|---|---|---|
| 8,114,601 B2 | 2/2012 | Bergeron et al. |
| 9,096,638 B2* | 8/2015 | Paquette ............... C07H 21/00 |
| 2009/0208948 A1 | 8/2009 | Paquette |

FOREIGN PATENT DOCUMENTS

| | | |
|---|---|---|
| JP | 2006333785 | 12/2006 |
| WO | WO 2008/041354 | 4/2008 |

OTHER PUBLICATIONS

Canadian Examination Report dated Mar. 15, 2016 in Canadian Application No. 2,698,232, filed Sep. 5, 2008.
Japanese Examination Report dated Nov. 24, 2015 in Japanese Application No. 2014-242047, filed Nov. 28, 2014.

(Continued)

*Primary Examiner* — Diana B Johannsen
(74) *Attorney, Agent, or Firm* — Knobbe Martens Olson and Bear, LLP

(57) ABSTRACT

Primers and probes for detection of toxin-producing (toxigenic) strains of *Clostridium difficile*, and to methods of detecting toxigenic strains using these primers and probes. Toxigenic strains of *C. difficile* are detected by nucleic acid-based amplification methods using particular primers and probes that bind to the toxin B (TcdB) gene. These primers and probes are used to amplify *C. difficile* nucleic acids in clinical samples to determine the presence of these toxigenic strains.

13 Claims, 3 Drawing Sheets

(56) References Cited

OTHER PUBLICATIONS

Abed et al., "Comparative study of three methods for cloning PCR products", World J Microbiol & Biotech. (Sep. 1995) 11(5): 478-480.
Alonso, R. et al. Toxigenic status of Clostridium difficile in a large Spanish teaching hospital. Journal of Medical Microbiology. Feb. 2005, vol. 54, Pt. 2, pp. 159-162, ISSN 0022-2615.
Belanger, S.D. et al. Rapid detection of Clostridium difficile in Feces by RealTime PCR. Journal of Clinical Microbiology. Feb. 2003, vol. 41, No. 2, pp. 730-734, ISSN 00951137.
Chaves-Olarte et al., A Novel Cytotoxin from Clostridium difficile Serogroup F is a Functional Hybrid between Two Other Large Clostridial Cytotoxins., J Biol Chem. (1999) 274(16): 1146-1152.
Cohen et al., Analysis of the Pathogenicity Locus in Clostridium difficile Strains, J. Infect. Dis. (2000) 181(2): 659-663.
Cohen et al., Isolation of a Toxin B-deficient Mutant Strain of Clostridium difficile in a Case of Recurrent C. difficile-associated Diarrhea., Clin Infect Dis. (1998) 26(2): 410-412.
Drudy et al., Toxin A-negative, Toxin B-positive Clostridium difficile., Int J Infect Dis. (2007) 11(1): 5-10.
GenBank Accession No. AJ011301, Kohl, "Clostridium difficile (strain 8864) pathogenicity DNA locus", Jan. 2001.
GenBank Accession No. X53138, Barroso et al., "Clostridium difficile toxB gene for toxin B", Apr. 2005.
GenBank Accession No. Z23277, von Eichel-Streiber et al., "C. difficile gene for toxin B", Apr. 2005.
Geric et al., Distribution of Clostridium difficile Variant Toxinotypes and Strains with Binary Toxin Genes among Clinical Isolates in an American Hospital., J Med Microbiol. (2004) 53(Pt9): 887-894.
Geric et al., Frequency of Binary Toxin Genes among Clostridium difficile Strains that do not Produce Large Clostridial Toxins., J Clin Microbiol. (2003) 41(11): 5227-5232.
Geric Stare et al., Variant Forms of the Binary Toxin CDT Locus and tcdC Gene in Clostridium difficile Strains., J Med Microbiol. (2007) 56(Pt 3): 329-335.
Goh et al., Effect of phage infection on toxin production by *Clostridium difficile*; J. Med. Microbiol., Feb. 2005; 54: 129-135.
Goh, S., "Phenotypic and genotypic characterization of bacteriophages of Clostridium difficile" Ph.D. Thesis, Australia 2003, Retrieved from the Internet: http://repository.uwa.edu.au/R/HLA2PK2H6KQRBNYXHMVPX6SMK9VYYXL4EPFXAADV73KE3NXALT-01439?func_results-full, retrieved on Mar. 23, 2011.
Kato et al., Identification of Toxin A-negative, Toxin B-positive Clostridium difficile by PCR., J Clin Microbiol. (1998) 36(8): 2178-2182.
Knoop et al., Clostridium difficile: Clinical Disease and Diagnosis., Clin Microbiol. Rev. (1993) 6(3): 251-265.
Kuijper et al., Emergence of Clostridium difficile-associated disease in North America and Europe, Clin Micro Infect., (2006) 12(supp6): 2-18.
Lee et al., "LuxS/autoinducer-2 quorum sensing molecule regulates transcriptional virulence gene expression in Clostridium difficile" Biochem and Biophysical Res Comm. (2005) 335: 659-666.
Lemee, L. et al. Multiplex PCR Targeting tpi (Triose Phosphate Isomerase), tcdA (Toxin A), and tcdB (Toxin B) Genes for Toxigenic Culture of Clostridium difficile. Journal of Clinical Microbiology. Dec. 2004, vol. 42, No. 12, pp. 5710- 5714, ISSN 0095-1137.

MacCannell et al., Characterization of a Novel, TcdB-deficient, NPA1 Variant Strain of Clostridium difficile., ICAAC 2006; University of Calgary, Canada, Faculty of Medicine; p. 1 [Abstract].
McDonald et al., An Epidemic, Toxin Gene-variant Strain of Clostridium difficile, N. Engl. J. Med. (2005) 353(23): 2433-2441.
Mehlig et al., Variant toxin B and a functional toxin A produced by Clostridium difficile C34, FEMS Microbiol. Lett. (2001) 198(2): 171-176.
Ott et al., "Quantification of intestinal bacterial populations by real-time PCR with a universal primer set and minor groove binder probes: a global approach to the enteric flora" J. Clin. Microbio. (2004) 42: 2566-2572.
Peterson, L.R. et al. Detection of Toxigenic Clostridium difficile in Stool Samples by Real-Time PCR for the Diagnosis of C. difficile-Associated Diarrhea. Clinical Infectious Diseases. Nov. 2007, vol. 45, No. 9, pp. 1152-1160, ISSN 1058-4838.
Plant-Mocrpbe Genomics Facility (PMGF) at the Ohio State University, "Procedures and Recommendations for Quantitative PCR", version 1.2, Apr. 2003.
Rupnik et al., A novel Toxinotyping Scheme and Correlation of Toxinotypes with Serogroups of Clostridium difficile Isolates. J Clin Microbiol (1998) 36(8): 2240-2247.
Rupnik et al., Characterization of polymorphisms in the toxin A and B genes of Clostridium difficile., FEMS Microbiol Lett. (1997) 148(2): 197-202.
Rupnik et al., Comparison of Toxinotyping and PCR Ribotyping of Clostridium difficile Strains and Dexcription of Novel Toxinotypes., Microbiology (2001) 147(Pt1): 439-447.
Rupnik et al., New types of Toxin A-negative, Toxin B-positive Strains among Clostridium difficile Isolates from Asia, J Clin Microbiol. (2003) 41(3): 1118-1125.
Rupnik et al., Revised nomenclature of Clostridium difficile toxins and associated genes., J Med Microbiol. (2005) 54: 113-117.
Van Den Berg et al., Rapid Diagnosis of Toxinogenic Clostridium difficile in Faecal Samples with Internally Controlled Real-time PCR. Clin Microbiol Infect. (2006) 12(2): 184-186.
Von Eichel-Streiber et al., Closing in on the toxic domain through analysis of a variant Clostridium difficile cytotoxin B., Mol Microbiol. (1995) 17(2): 313-321.
Von Eichel-Streiber et al., Comparative sequence analysis of the Clostridium difficile toxins A and B., Mol Gen Genet. (1992) 233(1-2): 260-268.
Voth et al., Clostridium difficile Toxins: Mechanism of Action and Role in Disease., Clin. Microbiol. Rev. (2005) 18(2): 247-263.
Australian Examination Report dated Jun. 21, 2013 in Australian Patent Application No. 2008295396, filed Sep. 5, 2008.
Australian 2nd Examination Report dated Dec. 11, 2014 in Australian Patent Application No. 2008295396, filed Sep. 5, 2008.
European Search Report, dated Mar. 23, 2011, issued in European patent application No. 08800272.
Extended European Search Report, dated May 20, 2011, issued in European patent application No. 08800272.
EPO Summons to Attend Oral Proceedings dated Sep. 19, 2013 in European Application No. 08800272.0.
International Search Report issued on the corresponding PCT Application No. PCT/CA2008/001564, dated Dec. 22, 2008.
International Preliminary Report on Patentability and Written Opinion dated Mar. 9, 2010 for PCT/CA2008/001564, filed Sep. 5, 2008.
Japanese Office Action dated Jul. 2, 2013 of Japanese Application No. 2010-523247, filed Sep. 5, 2008.
Canadian Examination Report dated Dec. 8, 2014 in Canadian Application No. 2,698,232, filed Sep. 5, 2008.

\* cited by examiner

5'-(FAM) CGG TTG TTG AAT TAG TAT CAA CTG CAC AAC CG (Dabcyl)- 3'

ΔG -4.33 kcal.mole- 1 (synthesis conditions)
ΔG -0.74 kcal.mole- 1 (PCR conditions)

5'-(TET) CGG GCG ATG CCT CTT CAC ATT GCT CCA CCT TTC CTC GCC GG (Dabcyl)- 3'

ΔG -5.84 kcal.mole- 1 (synthesis conditions)
ΔG -1.83 kcal.mole- 1 (PCR conditions)

SEQUENCE LISTING

```
<160> NUMBER OF SEQ ID NOS: 33

<210> SEQ ID NO 1
<211> LENGTH: 7110
<212> TYPE: DNA
<213> ORGANISM: Clostridium difficile

<400> SEQUENCE: 1
attttatgag tttagttaat agaaaacagt tagaaaaaat ggcaaatgta agatttcgta      60
ctcaagaaga tgaatatgtt gcaatattgg atgctttaga agaatatcat aatatgtcag     120
agaatactgt agtcgaaaaa tatttaaaat taaaagatat aaatagttta acagatattt     180
atatagatac atataaaaaa tctggtagaa ataaagcctt aaaaaaattt aaggaatatc     240
tagttacaga agtattagag ctaaagaata ataatttaac tccagttgag aaaaatttac     300
attttgtttg gattggaggt caaataaatg acactgctat taattatata aatcaatgga     360
aagatgtaaa tagtgattat aatgttaatg ttttttatga tagtaatgca tttttgataa     420
acacattgaa aaaaactgta gtagaatcag caataaatga tacacttgaa tcatttagag     480
aaaacttaaa tgaccctaga tttgactata ataaattctt cagaaaacgt atggaaataa     540
tttatgataa acagaaaaat ttcataaact actataaagc tcaaagagaa gaaatcctg      600
```

```
aacttataat tgatgatatt gtaaagacat atctttcaaa tgagtattca aaggagatag    660
atgaacttaa tacctatatt gaagaatcct taaataaaat tacacagaat agtggaaatg    720
atgttagaaa ctttgaagaa tttaaaaatg gagagtcatt caacttatat gaacaagagt    780
tggtagaaag gtggaattta gctgctgctt ctgaagtcta tagagaaacc tagttcagta    840
acagtggatt tttgggaaat gacaaagtta gaagctataa tgaaatacaa agaatatata    900
ccagaatata cctccatatt aagaatatct gcattaaaag aaattggtgg tatgtattta    960
gatgttgata tgttaccagg aatacaacca gacttatttg agaacatttt gacatgttag    1020
acgaagaagt tcaaagtagt tttgaatctg ttctagcttc taagtcagat aaatcagaaa    1080
tattctcatc acttggtgat atggaggcat caccactaga agttaaaatt gcatttaata    1140
gtaagggtat tataaatcaa gggctaattt ctgtgaaaga ctcatattgt agcaatttaa    1200
tagtaaaaca aatcgagaat agatataaaa tattgaataa tagtttaaat ccagctatta    1260
gcgaggataa tgattttaat actacaacga atacctttat tgatagtata atggctgaag    1320
ctaatgcaga taatggtaga tttatgatgg aactaggaaa gtatttaaga gttggtttct    1380
tcccagatgt taaaactact attaacttaa gtggccctga agcatatgcg gcagcttatc    1440
aagatttatt aatgttaaa gaaggcagta tgaatatcca tttgatagaa gctgatttaa    1500
gaaactttga atctctaaa actaatattt ctcaatcaac tgaacaagaa atggctagct    1560
tatggtcatt tgacgatgca agagctaaag ctcaatttga agaatataaa aggaattatt    1620
ttgaaggttc tcttggtgaa gatgataatc ttgatttttc tcaaaatata gtagttgaca    1680
aggagtatct tttagaaaaa atatcttcat tagcaagaag ttcagagaga ggatatatac    1740
actatattgt tcagttacaa ggagataaaa ttagttatga agcagcatgt aacttatttg    1800
caaagactcc ttatgatagt gtactgtttc agaaaaatat agaagattca gaaattgcat    1860
attattataa tcctggagat ggtgaaatac aagaaataga caagtataaa attccaagta    1920
taatttctga tagacctaag attaaattaa catttattgg tcatggtaaa gatgaattta    1980
atactgatat atttgcaggt tttgatgtag attcattatc cacagaaata gaagcagcaa    2040
tagatttagc taaagaggat atttctccta agtcaataga aataaattta ttaggatgta    2100
atatgtttag ctactctatc aacgtagagg agacttatcc tggaaaatta ttacttaaag    2160
ttaaagataa aatatcagaa ttaatgccat ctataagtca agactctatt atagtaagtg    2220
caaatcaata tgaagttaga ataaatagtg aaggaagaag agaattattg gatcattctg    2280
gtgaatggat aaataaagaa gaaagtatta taaaggatat ttcatcaaaa gaatatatat    2340
catttaatcc taaagaaaat aaaattacag taaaatctaa aaatttaccct gagctatcta    2400 cattattaca agaaattaga aataattcta attcaagtga tattgaacta gaagaaaaag    2460
taatgttaac agaatgtgag ataaatgtta tttcaaatat agatacgcaa attgttgagg    2520
aaaggattga agaagctaag aatttaactt ctgactctat taattatata aaagatgaat    2580
ttaaactaat agaatctatt tctgatgcac tatgtgactt aaaacaacag aatgaattag    2640
aagattctca ttttatatct tttgaggaca tatcagagac tgatgaggga tttagtataa    2700 gattattaa taaagaaact ggagaatcta tatttgtaga aactgaaaaa acaatattct    2760
ctgaatatgc taatcatata actgaagaga tttctaagat aaaaggtact atatttgata    2820
ctgtaaatgg taagttagta aaaaaagtaa atttagatac tacacacgaa gtaaatactt    2880
taaatgctgc attttttata caatcattaa tagaatataa tagttctaaa gaatctctta    2940
gtaatttaag tgtagcaatg aaagtccaag tttacgctca attatttagt actggtttaa    3000
```

```
atactattac agatgcagcc aaagttgttg aattagtatc aactgcatta gatgaaacta    3060
tagacttact tcctacatta tctgaaggat tacctataat tgcaactatt atagatggtg    3120
taagtttagg tgcagcaatc aaagagctaa gtgaaacgag tgacccatta ttaagacaag    3180
aaatagaagc taagataggt ataatggcag taaatttaac aacagctaca actgcaatca    3240
ttacttcatc tttggggata gctagtggat ttagtatact tttagttcct ttagcaggaa    3300
tttcagcagg tataccaagc ttagtaaaca atgaacttgt acttcgagat aaggcaacaa    3360
aggttgtaga ttattttaaa catgtttcat tagttgaaac tgaaggagta tttactttat    3420
tagatgataa aataatgatg ccacaagatg atttagtgat atcagaaata gattttaata    3480
ataattcaat agttttaggt aaatgtgaaa tctggagaat ggaaggtggt tcaggtcata    3540
ctgtaactga tgatatagat cacttctttt cagcaccatc aataacatat agagagccac    3600
acttatctat atatgacgta ttggaagtac aaaaagaaga acttgatttg tcaaaagatt    3660
taatggtatt acctaatgct ccaaatagag tatttgcttg ggaaacagga tggacaccag    3720
gtttaagaag cttagaaaat gatggcacaa aactgttaga ccgtataaga gataactatg    3780
aaggtgagtt ttattggaga tattttgctt ttatagctga tgcttttaata acaacattaa    3840 aaccaagata tgaagatact aatataagaa taaatttaga tagtaatact agaagtttta    3900
tagttccaat aataactaca gaatatataa gagaaaaatt atcatattct ttctatggtt    3960
caggaggaac ttatgcattg tctctttctc aatataatat gggtataaat atagaattaa    4020
gtgaaagtga tgtttggatt atagatgttg ataatgttgt gagagatgta actatagaat    4080
ctgataaaat taaaaaaggt gatttaatag aaggtatttt atctacacta agtattgaag    4140
agaataaaat tatcttaaat agccatgaga ttaattttc tggtgaggta aatggaagta    4200
atggatttgt ttctttaaca ttttcaattt tagaaggaat aaatgcaatt atagaagttg    4260
atttattatc taaatcatat aaattactta tttctggcga attaaaaata ttgatgttaa    4320
attcaaatca tattcaacag aaaatagatt atataggatt caatagcgaa ttacagaaaa    4380
atataccata tagctttgta gatagtgaag gaaagagaa tggttttatt aatggttcaa    4440
caaaagaagg tttatttgta tctgaattac ctgatgtagt tcttataagt aaggtttata    4500
tggatgatag taagccttca tttggatatt atagtaataa tttgaaagat gtcaaagtta    4560
taactaaaga taatgttaat atattaacag gttattatct taaggatgat ataaaaatct    4620
ctctttcttt gactctacaa gatgaaaaaa ctataaagtt aaatagtgtg catttagatg    4680
aaagtggagt agctgagatt ttgaagttca tgaatagaaa aggtaataca aatacttcag    4740
attctttaat gagcttttta gaaagtatga atataaaaag tattttcgtt aatttcttac    4800 aatcaatat taagtttata ttagatgcta attttataat aagtggtact acttctattg    4860
gccaatttga gtttatttgt gatgaaaatg ataatataca accatatttc attaagttta    4920
atacactaga aactaattat actttatatg taggaaatag acaaaatatg atagtggaac    4980
caaattatga tttagatgat tctggagata tatcttcaac tgttatcaat ttctctcaaa    5040
agtatcttta tggaatagac agttgtgtta ataaagttgt aatttcacca aatatttata    5100
cagatgaaat aaatataacg cctgtatatg aaacaaataa tacttatcca gaagttattg    5160
tattagatgc aaattatata aatgaaaaaa taaatgttaa tatcaatgat ctatctatac    5220
gatatgtatg gagtaatgat ggtaatgatt ttattcttat gtcaactagt gaagaaaata    5280
aggtgtcaca agttaaaata agattcgtta atgttttaa agataagact ttggcaaata    5340
```

-continued

```
agctatcttt taactttagt gataaacaag atgtacctgt aagtgaaata atcttatcat    5400
ttacaccttc atattatgag gatggattga ttggctatga tttgggtcta gtttctttat    5460
ataatgagaa attttatatt aataactttg gaatgatggt atctggatta atatatatta    5520
atgattcatt atattatttt aaaccaccag taaataattt gataactgga tttgtgactg    5580
taggcgatga taaatactac tttaatccaa ttaatggtgg agctgcttca attggagaga    5640
caataattga tgacaaaaat tattatttca accaaagtgg agtgttacaa acaggtgtat    5700
ttagtacaga agatggattt aaatattttg ccccagctaa tacacttgat gaaaacctag    5760
aaggagaagc aattgatttt actgaaaaat taattattga cgaaaatatt tattattttg    5820
atgataatta tagaggagct gtagaatgga agaattaga tggtgaaatg cactatttta    5880
gcccagaaac aggtaaagct tttaaaggtc taaatcaaat aggtgattat aaatactatt    5940
tcaattctga tggagttatg caaaaaggat ttgttagtat aaatgataat aaacactatt    6000
ttgatgattc tggtgttatg aaagtaggtt acactgaaat agatggcaag catttctact    6060
ttgctgaaaa cggagaaatg caaataggag tatttaatac agaagatgga tttaaatatt    6120
ttgctcatca taatgaagat ttaggaaatg aagaaggtga agaaatctca tattctggta    6180
tattaaattt caataataaa atttactatt ttgatgattc atttacagct gtagttggat    6240
ggaaagattt agaggatggt tcaaagtatt attttgatga agatacagca gaagcatata    6300
taggtttgtc attaataaat gatggtcaat attattttaa tgatgatgga attatgcaag    6360
ttggatttgt cactataaat gataaagtct tctacttctc tgactctgga attatagaat    6420
ctggagtaca aaacatagat gacaattatt tctatataga tgataatggt atagttcaaa    6480
ttggtgtatt tgatacttca gatggatata atatttttgc acctgctaat actgtaaatg    6540
ataaatttta cggacaagca gttgaatata gtggtttagt tagagttggg gaagatgtat    6600
attattttgg agaaacatat acaattgaga ctggatggat atatgatatg gaaaatgaaa    6660
gtgataaata ttatttcaat ccagaaacta aaaaagcatg caaaggtatt aatttaattg    6720
atgatataaa atattatttt gatgagaagg gcataatgag aacgggtctt atatcatttg    6780
aaaataataa ttattacttt aatgagaatg gtgaaatgca atttggttat ataaatatag    6840
aagataagat gttctatttt ggtgaagatg gtgtcatgca gattggagta tttaatacac    6900
cagatggatt taaatacttt gcacatcaaa atacttggaa tgagaatttt gagggagaat    6960
caataaacta tactggttgg ttagatttag atgaaaagag atattatttt acagatgaat    7020
atattgcagc aactggttca gttattattg atggtgagga gtattatttt gatcctgata    7080
cagctcaatt agtgattagt gaatagataa                                      7110
```

<210> SEQ ID NO 2
<211> LENGTH: 7013
<212> TYPE: DNA
<213> ORGANISM: Clostridium difficile

<400> SEQUENCE: 2

```
atgagtttag ttaatagaaa acagttagaa aaaatggcaa atgtaagatt tcgtgttcag      60
gaagatgaat atgtagcaat attagatgca ttagaagaat atcataatat gtcagaaaat     120
actgtagttg aaaagtatct aaaattaaaa gatataaaca gtttaacaga tacttatata     180
gatacatata aaaaatctgg tcgaaataaa gccttaaaaa aatttaaaga gtacttagtt     240
ataagagatat tagaattaga agaatagcaa tttaactcca gtcgagaaaa atttacattt     300
tatatggatt ggagggcaaa taaatgatac tgctattaat tatataaatc aatggaaaga     360
```

```
tgtaaatagt gactataatg ttaatgtttt ttatgatagt aatgcatttt aaccacactg    420
caattttcag aaaacgtatg caaataactt atgataaaca gcaaatttc ataaattact    480 ataaagctca aaaagaagaa atcctgtttt tgataaacac attgaaaaaa actataatag    540
aatcagcatc aaatgatacc cttgaatcat ttagagaaaa tttaaatgat cctgaaacct    600
tataattgat gatattgtaa agacatatct ttcaaacgag tattcaaagg atatagatga    660
acttaatgct tatattgaag agtcattaaa caaagtcaca gaaaatagtg gaaatgatgt    720
tagaaacttt gaagaattta aaactggaga agtattcaat ttatatgaac aagagttagt    780
agaaagatgg aatcttgctg gtgcatctga tatattaaga gtcgctatat tgaaaaatat    840
tggtggagtc tatctagatg ttgatatgtt accaggaata cacccagatt tatttaaaga    900
tataaataag cctgattcag taaagacagc tgtagatttg ggaagagatg cagttagaag    960
ccataatgaa acataaagaa tatataccag aatatacttc gaaacatttt gatacattgg   1020
atgaagaagt tcaaagtagc tttgaatctg ttttagcttc taagtctgat aagtcagaaa   1080
tatttttacc actaggagat atagaggtat caccttttaga agtaaaaatt gcatttgcca   1140
aaggttctat tataaatcaa gctctaattt ctgcaaaaga ttcatattgt agtgacttac   1200
taataaaaca aatccaaaac agatataaga tactgaatga tactttaggt ccagctatta   1260
gtcaaggtaa tgattttaat actacaatga acaattttgg tgaaagtttg ggagctatag   1320
ctaatgaaga gaatataagt tttatagcaa aaatcggaag ttatttaagg gttggatttt   1380
atcctgaagc taatactaca gttactttaa gtggtcctac aatatatgca ggagcttata   1440
aagatttatt aacatttaaa gagatgagca atagatactt ctatattgtc gatctgagtt   1500
aagaaatttt gaatttccta aggttaatat atctcaagca acagaacaag agaaaaatag   1560
tttatggcaa tttaatgaag aaaagagctaa aattcaattt gaagaataca agaaaaatta   1620
ttttgaaggt gcacttggag aagatgataa tcttgatttt tctcaaaata cagtaactga   1680
caaagaatat cttttagaaa agatctcttc atcaacgaag aagttcagaa agaggatatg   1740
ttcattatat tgttcaatta caaggagata aaattagcta tgaagcagca tgtaacttat   1800
ttgcaaaaaa tccttatgac agtatactat ttcaaaaaaa tatagaagat tcagaagtag   1860
catattacta taatcctaca gatagtgaaa tacaagaaat tgataagtat agaattcctg   1920
atagaatctc tgatagacct aagattaaat taacattcat tggtcatggc aaagctgaat   1980
ttaatactga tatatttgca ggtcttgatg tagattcatt atcttcagaa atagaaacag   2040
caataggttt agccaaagag gatatttctc ctaaatctat agaaataaac ttactgggat   2100
gtaacatgtt tagctattct gtaaatgtag aagagactta tcctgggaaa ttattactta   2160
gagttaaaga taaagtatca gaattaatgc catctatgag tcaagactct attatagtaa   2220
gtgcaaatca atatgaagtt agaataaata gtgaaggaag aagagaatta ttagaccatt   2280
ctggtgaatg gataaacaaa gaagaaagta ttataaagga tatttcatca aaagaatata   2340
tatcatttaa tcctaaagag aataaagtta tagtaaaatc taaaaattta cctgaattat   2400
ctacattatt acaagaaatt agaataattc taattcaag tgatattgaa ctagaagaaa   2460
aagtaatgtt agcagaatgt gagataaatg ttatttcaaa tatagagaca caagtggtag   2520
aagaaagaat tgaagaagct aaaagcttaa cttctgactc tattaattat ataaagaatg   2580
aatttaaact aatagaatct atttctgatg cactatgtga cttaaaacaa cagaatgaat   2640
tagaagattc tcatttttata tcttttgagg acatatcaga gactgatgag gggtttagta   2700
```

-continued

```
taagatttat taataaagaa actggagaat ctatatttgt agaaactgaa aaacaatat    2760
tctctgaata tgctaatcat ataactgaag agatttctaa gataaaaggt actatatttg   2820
atactgtaaa tggtaagtta gtaaaaaaag taaatttaga tactacacac gaagtaaata   2880
ctttaaatgc tgcattttt atacaatcat taatagaata taatagttct aaagaatctc    2940
ttagtaattt aagtgtagca atgaaagttc aagtttacgc tcaattattt agtactggtt   3000
taaatactat tacagatgca gccagagttg ttgaattagt atcaactgca ttagatgaaa   3060
ctatagactt acttcctaca ttatctgaag gattacctat aattgcaact attatagatg   3120
gtgtaagttt aggtgcagca atcaaagagc taagtgaaac gagtgaccca ttattaagac   3180
aagaaataga agctaagata ggtataatgg cagtaaattt aacaacagct acaactgcaa   3240
tcattacttc atctttgggg atagctagtg gatttagtat acttttagtt cctttagcag   3300
gaatttcagc aggtatacca agcttagtaa acaatgaact tgtacttcga gataaggcaa   3360
caaaggttgt agattatttt aaacatgtt cattagttga aactgaagga gtatttactt    3420
tattagatga taaagtaatg atgccacaag atgatttagt gatatcagaa atagatttta   3480
ataataattc aatagtttta ggtaaatgtg aaatctggag aatggaaggt ggttcaggtc   3540
atactgtaac tgatgatata gatcacttct tttcagcacc atcaataaca tatagagagc   3600
cacacttatc tatatatgac gtattggaag tacaaaaaga agaacttgat ttgtcaaaag   3660
atttaatggt attacctaat gctccaaata gagtatttgc ttgggaaaca ggatggacac   3720
caggtttaag aagcttagaa aatgatggca caaaactgtt agaccgtata agagataact   3780
atgaaggtga gttttattgg agatatttg ctttttatagc tgatgcttta ataacaacat    3840
taaaaccaag atatgaagat actaatataa gaataaattt agatagtaat actagaagtt   3900
ttagggtata aatatagaat taagtgaaag tgatgtttgg attatagatg ttgataatgt   3960
tgtgagagat gtaactatag aatctgataa aattaaaaaa ggtgatttaa tagaaggtat   4020
tttatctaca ctaagtattg aagagaataa aattatctta aatagccatg agattaattt   4080
ttctggtgag gtaaatggaa gtaatggatt tgtttcttta acattttcaa ttttagaagg   4140
aataaatgca attatagaag ttgatttatt atctaaatca tataaattac ttatttctgg   4200
cgaattaaaa atattgatgt taaattcaaa tcatattcaa cagaaaatag attatatagg   4260
attcaatagc gaattacaga aaaatatacc atatagcttt gtagatagtg aaggaaaaga   4320
gaatggtttt attaatggtt caacaaaaga aggtttattt gtatctgaat tacctgatgt   4380
agttcttata agtaaggttt atatggatga tagtaagcct tcatttggat attatagtaa   4440
taatttgaaa gatgtcaaag ttataactaa agataatgtt aatatattaa caggttatta   4500
tcttaaggat gatataaaaa tctctctttc tttgactcta caagatgaaa aaactataaa   4560
gttaaatagt gtgcatttag atgaaagtgg agtagctgag attttgaagt tcatgaatag   4620
aaaaggtagt acaaatactt cagattcttt aatgagcttt ttagaaagta tgaatataaa   4680
aagtattttc gttaatttct tacaatctaa tattaagttt atattagatg ctaatttat    4740
aataagtggt actacttcta ttggccaatt tgagtttatt tgtgatgaaa ataataatat   4800
acaaccatat tcattaagt ttaatacact agaaactaat tatactttat atgtaggaaa    4860
tagacaaaat atgatagtgg aaccaaatta tgatttagat gattctggag atatatcttc   4920
aactgttatc aatttctctc aaaagtatct ttatggaata gacagttgtg ttaataaagt   4980
tgtaatttca ccaaatattt atacagatga aataaatata acgcctgtat atgaaacaaa   5040
taatacttat ccagaagtta ttgtattaga tgcaaattat ataaacgaaa aaataaatgt   5100
```

```
taatatcaat gatctatcta tacgatatgt atggagtaat gatggtaatg attttattct    5160
tatgtcaact agtgaagaaa ataaggtgtc acaagttaaa ataagattcg ttaatgtttt    5220
taaagataag actttggcaa ataagctatc ttttaactt agtgataaac aagatgtacc     5280
tgtaagtgaa ataatcttat catttacacc ttcatattat gaggatggat tgattggcta    5340
tgatttgggt ctagtttctt tatataatga gaaattttat attaataact ttggaatgat    5400
ggtatctgga ttaatatata ttaatgattc attatattat tttaaaccac cagtaaataa    5460
tttgataact ggatttgtga ctgtaggcga tgataaatac tactttaatc caattaatgg    5520
tggagctgct tcaattggag agacaataat tgatgacaaa aattattatt caaccaaag    5580 tggagtgtta caaacaggtg tatttagtac agaagatgga tttaaatatt ttgccccagc    5640
taatacactt gatgaaaacc tagaaggaga agcaattgat tttactggaa aattaattat    5700
tgacgaaaat atttattatt ttgaagataa ttatagagga gctgtagaat ggaaagaatt    5760
agatggtgaa atgcactatt ttagcccaga aacaggtaaa gcttttaaag gtctaaatca    5820
aataggtgat gataaatact atttcaattc tgatggagtt atgcaaaaag gatttgttag    5880
tataaatgat aataaacact atttttgatga ttctggtgtt atgaaagtag gttacactga    5940
aatagatggc aagcatttct actttgctga aaacggagaa atgcaaatag gagtatttaa    6000
tacagaagat ggatttaaat attttgctca tcataatgaa gatttaggaa atgaagaagg    6060
tgaagaaatc tcatattctg gtatattaaa tttcaataat aaaatttact attttgatga    6120
ttcatttaca gctgtagttg gatggaaaga tttagaggat ggttcaaagt attatttga    6180 tgaagataca gcagaagcat atataggttt gtcattaata aatgatggtc aatattattt    6240
taatgatgat ggaattatgc aagttggatt tgtcactata aatgataaag tcttctactt    6300
ctctgactct ggaattatag aatctggagt acaaaacata gatgacaatt atttctatat    6360
agatgataat ggtatagttc aaattggtgt atttgatact tcagatggat ataaatattt    6420
tgcacctgct aatactgtaa atgataatat ttacggacaa gcagttgaat atagtggttt    6480
agttagagtt ggtgaagatg tatattattt tggagaaaca tatacaattg agactggatg    6540
gatatatgat atggaaaatg aaagtgataa atattatttc gatccagaaa ctaaaaaagc    6600
atgcaaaggt attaatttaa ttgatgtatt aaaatattat tttgatgaga agggcataat    6660
gagaacgggt cttatatcat ttgaaaataa taattattac tttaatgaga atggtgaaat    6720
gcaatttggt tatataaata tagaagataa gatgttctat tttggtgaag atggtgtcat    6780
gcagattgga gtatttaata caccagatgg atttaaatac tttgcacatc aaaatacttt    6840
ggatgagaat tttgagggag aatcaataaa ctatactggt tggttagatt tagatgaaaa    6900
gagatatatt tttacagatg aatatattgc agcaactggt tcagttatta ttgatggtga    6960
ggagtattat tttgatcctg atacagctca attagtgatt agtgaataga taa           7013
```

<210> SEQ ID NO 3
<211> LENGTH: 7010
<212> TYPE: DNA
<213> ORGANISM: Clostridium difficile

<400> SEQUENCE: 3

```
atgagtttag ttaatagaaa acagttagaa aaaatggcaa atgtaagatt cgtgttcag      60 gaagatgaat atgtagcaat attagatgca ttagaagaat atcataatat gtcagaaaat     120
actgtagttg aaaagtatct aaaattaaaa gatataaaca gtttaacaga tacttatata    180
```

```
gatacatata aaaaatctgg tcgaaataaa gccttaaaaa aatttaaaga gtacttagtt      240
atagagatat tagaattaaa aaatagcaat ttaactccag tcgagaaaaa tttacatttt      300
atatggattg gagggcaaat aaatgatact gctattaatt atataaatca atggaaagat      360
gtaaatagtg actataatgt taatgttttt tatgatttaa ccacactgca attttcagaa      420
aacgtatgca ataatctat gataaacagc aaaatttcat aaattactat aaagctcaaa       480
aagaagaaaa tcctgacctt ataattgatg atattgtaaa gacatatctt tcaaacgagt      540
attcaaagga tatagatgaa cttaatgctt atattgaaga gtcattaaac aaagtcacag      600
aaaatagtgg aaatgatgtt agaaactttg aagaatttaa aactggagaa gtattcaatt      660
tatatgaaca agagtcagta gaaagatgga atcttgctgg tgcatctgat atattaagag      720
tcgctatatt gaaaaatatt ggtggagtct atctagatgt tgatatgtta ccaggaatac      780
acccagattt atttaaagat ataaataagc ctgattcagt aaagacagct gtagatttgg      840
gaagagatgc agttagaagc cataatgaaa cataaagaat atataccaga atatacttcg      900
aaacattttg atacattgga tgaagaagtt caaagtagct ttgaatctgt tttagcttct      960
aagtctgata agtcagaaat attttttacca ctaggagata tagaggtatc acctttagaa     1020
gtaaaaattg catttgccaa aggttctatt ataaatcaag ctctaatttc tgcaaaagat      1080
tcatattgta gtgacttact aataaaacaa atccaaaaca gataagat actgaatgat        1140 actttaggtc caattattag tcaaggtaat gatttttaata ctacaatgaa caattttggt     1200
gaaagtttgg gagctatagc taatgaagag aatataagtt ttatagcaaa aatcggaagt     1260
tatttaaggg ttggattta tcctgaagct aatactacat tactttaagt ggtcctacaa      1320
tatatgcagg agcttataaa gattattaa catttaaaga gatgagcata gatacttcta      1380
tattgtcgat ctgagttaag aaattttgaa tttcctaagg ttaatatatc tcaagcaaca     1440
gaacaagaga aaaatagttt atggcaattt aatgaagaaa gagctaaaat tcaatttgaa      1500
gaatacaaga aaaattattt tgaaggtgca cttggagaag atgataatct tgattttct       1560 caaaatacag taactgacaa agaatatctt ttagaaaaga tctcttcatc aacgaagaag      1620
ttcagaaaga ggatatgttc attatattgt tcaattacaa ggagataaaa ttagctatga      1680
agcagcatgt aacttatttg caaaaaatcc ttatgacagt atactatttc aaagaaatat      1740
agaagattca gaagtagcat attactataa tcctacagat agtgaaatac aagaaattga      1800
taagtataga attcctgata gaatctctga tagacctaag attaaattaa cattcattgg      1860
tcatggcaaa gctgaattta atactgatat atttgcaggt cttgatgtag attcattatc      1920
ttcagaaata gaaacagcaa taggtttagc caaagaggat atttctccta aatctataga      1980
aataaactta ctgggatgta acatgtttag ctattctgta aatgtagaag agacttatcc      2040
tgggaaatta ttacttagag ttaaagataa agtatcagaa ttaatgccat ctatgagtca     2100
agactctatt atagtaagtg caaatcaata tgaagttaga ataaatagtg aaggaagaag      2160
agaattatta gaccattctg gtgaatggat aaacaaagaa gaaagtatta taaaggatat      2220
ttcatcaaaa gaatatatat catttaatcc taaagagaat aaaattatag taaaatctaa      2280
aaatttacct gaattatcta cattattaca agaaattaga aataattcta attcaagtga      2340
tattgaacta gaagaaaaag taatgttagc agaatgtgag ataaatgtta tttcaaatat      2400
agagacacaa gtggtagaag aaagaattga agaagctaaa agcttaactt ctgactctat      2460
taattatata aagaatgaat ttaaactaat agaatctatt tctgaggcac tatgtgactt      2520
aaaacaacag aatgaattag aagattctca tttatatct tttgaggaca tatcagagac      2580
```

```
tgatgagggg tttagtataa gatttattaa taaagaaact ggagaatcta tatttgtaga    2640
aactgaaaaa acaatattct ctgaatatgc taatcatata actgaagaga tttctaagat    2700
aaaaggtact atatttgata ctgtaaatgg taagttagta aaaaaagtaa atttagatac    2760
tacacacgaa gtaaatactt taaatgctgc attttttata caatcattaa tagaatataa    2820
tagttctaaa gaatctctta gtaatttaag tgtagcaatg aaagttcaag tttacgctca    2880
attatttagt actggtttaa atactattac agatgcagcc agagttgttg aattagtatc    2940
aactgcatta gatgaaacta tagacttact tcctacatta tctgaaggat tacctataat    3000
tgcaactatt atagatggtg taagtttagg tgcagcaatc aaagagctaa gtgaaacgag    3060
tgacccatta ttaagacaag aaatagaagc taagataggt ataatggcag taaatttaac    3120
aacagctaca actgcaatca ttacttcatc tttggggata gctagtggat ttagtatact    3180
tttagttcct ttagcaggaa tttcagcagg tataccaagc ttagtaaaca atgaacttgt    3240
acttcgagat aaggcaacaa aggttgtaga ttattttaaa catgtttcat tagttgaaac    3300
tgaaggagta tttactttat tagatgataa agtaatgatg caacaagatg atttagtgat    3360
atcagaaata gattttaata ataattcaat agttttaggt aaatgtgaaa tctggagaat    3420
ggaaggtggt tcaggtcata ctgtaactga tgatatagat cacttctttt cagcaccatc    3480
aataacatat agagagccac acttatctat atatgacgta ttggaagtac aaaaagaaga    3540
acttgatttg tcaaaagatt taatggtatt acctaatgct ccaaatagag tatttgcttg    3600
ggaaacagga tggacaccag gtttaagaag cttagaaaat gatggcacaa aactgttaga    3660
ccgtataaga gataactatg aaggtgagtt ttattggaga tattttgctt ttatagctga    3720
tgctttaata acaacattaa aaccaagata tgaagatact aatataagaa taaatttaga    3780
tagtaatact agaagttta tagttccaat aataactaca gaatatataa gagaaaaatt    3840
atcatattct ttctatggtt caggaggaac ttatgcattg cctctttctc aatataatat    3900
gggtataaat atagaattaa gtgaaagtga tgtttggatt atagatgttg ataatgttgt    3960
gagagatgta actatagaat ctgataaaat taaaaaaggt gatttaatag aaggtatttt    4020
atctacacta agtattgaag agaataaaat tatcttaaat agccatgaga ttaatttttc    4080
tggtgaggta aatggaagta atggatttgt ttctttaaca ttttcaattt tagaaggaat    4140
aaatgcaatt atagaagttg atttattatc taaatcatat aaattactta tttctggcga    4200
attaaaaata ttgatgttaa attcaaatca tattcaacag aaaatagatt ataataggatt    4260 caatagcgaa ttacagaaaa atataccata tagctttgta gatagtgaag gaaaagaaa    4320 tggttttatt aatggttcaa caaaagaagg tttatttgta tcagaattac ctgatgtagt    4380
tcttataagt aaggtttata tggatgatag taagccttca tttggatatt atagtaataa    4440
tttgaaagat gtcaaagtta taactaaaga taatgttaat atattaacag gttattatct    4500
taaggatgat ataaaaatct ctcttttcttt gactctacaa gatgaaaaaa ctataaagtt    4560
aaatagtgtg catttagatg aaagtggagt agctgagatt ttgaagttca tgaatagaaa    4620
aggtagtaca aatacttcag attctttaat gagcttttta gaaagtatga atataaaaag    4680
tattttcgtt aatttcttac aatctaatat taagtttata ttagatgcta attttataat    4740
aagtggtact acttctattg gccaatttga gtttatttgt gatgaaaata ataatataca    4800
accatatttc attaagttta atacactaga aactaattat actttatatg taggaaatag    4860
acaaaatatg atagtggaac caaattatga tttagatgat tctggagata tatcttcaac    4920
```

```
tgttatcaat ttctctcaaa agtatcttta tggaatagac agttgtgtta ataaagttgt      4980
aatttcacca atatttata cagatgaaat aaataacg cctgtatatg aaacaaataa          5040
tacttatcca gaagttattg tattagatgc aaattatata acgaaaaaa taaatgttaa        5100 tatcaatgat ctatctatac gatatgtatg gagtaatgat ggtaatgatt ttattcttat       5160
gtcaactagt gaagaaaata aggtgtcaca agttaaaata agattcgtta atgtttttaa       5220
agataagact ttggcaaata agctatcttt taactttagt gataaacaag atgtacctgt       5280
aagtgaaata atcttatcgt ttacaccttc atattatgag gatggattga ttggctatga      5340
tttgggtcta gtttctttat ataatgagaa attttatatt ataactttg gaatgatggt       5400 atctggatta atatatatta atgattcatt atattatttt aaaccaccag taaataattt      5460
gataactgga tttgtgactg taggcgatga taaatactac tttaatccaa ttaatggtgg      5520
agctgcttca attggagaga caataattga tgacaaaaat tattatttca accaaagtgg      5580
agtgttacaa acaggtgtat ttagtacaga agatggattt aaatattttg ccccagctaa      5640
tacacttgat gaaaacctag aaggagaagc aattgatttt actggaaaat taattattga      5700
cgaaaatatt tattatttg aagataatta tagaggagct gtagaatgga agaattaga        5760 tggtgaaatg cactatttta gcccagaaac aggtaaagct tttaaaggtc taaatcaaat      5820
aggtgatgat aaatactatt tcaattctga tggagttatg caaaaaggat ttgttagtat      5880
aaatgataat aaacactatt ttgatgattc tggtgttatg aaagtaggtt acactgaaat      5940
agatggcaag catttctact ttgctgaaaa cggagaaatg caaataggag tatttaatac      6000
agaagatgga tttaaatatt ttgctcatca taatgaagat ttaggaaatg aagaaggtga      6060
agaaatctca tattctggta tattaaattt caataataaa atttactatt ttgatgattc      6120
atttacagct gtagttggat ggaaagattt agaggatggt tcaaagtatt attttgatga      6180
agatacagca gaagcatata taggtttgtc attaataaat gatggtcaat attatttttaa     6240 tgatgatgga attatgcaag ttggatttgt cactataaat gataaagtct tctacttctc      6300
tgactctgga attatagaat ctggagtaca aaacatagat gacaattatt tctatataga      6360
tgataatggt atagttcaaa ttggtgtatt tgatacttca gatggatata aatatttgc        6420 acctgctaat actgtaaatg ataatattta cggacaagca gttgaatata gtggtttagt      6480
tagagttggt gaagatgtat attattttgg agaaacatat acaattgaga ctggatggat      6540
atatgatatg gaaaatgaaa gtgataaata ttatttcgtt ccagaaacta aaaaagcatg      6600
caaaggtatt aatttaattg atgatataaa atatttttt gatgagaagg gcataatgag      6660
aacgggtctt atatcatttg aaaataataa ttattacttt aatgagaatg gtgaaatcca      6720
atttggttat ataaatatag aagataagat gttctatttt ggtgaagatg gtgtcatgca      6780
gattggagta tttaatacac cagatggatt taaaatacttt gcacatcaaa atactttgga      6840
tgagaatttt gagggagaat caataaacta tactggttgg ttaggtttag atgaaaagag      6900
atattatttt acagatgaat atattgcagc aactggttca gttattattg atggtgagga      6960
gtattatttt gatcctgata cagctcaatt agtgattagt gaatagataa                  7010
```

<210> SEQ ID NO 4
<211> LENGTH: 7111
<212> TYPE: DNA
<213> ORGANISM: Clostridium difficile

<400> SEQUENCE: 4

```
atgagtttag ttaatagaaa acagttagaa aaaatggcaa atgtaagatt tcgtgttcag      60
```

```
gaagatgaat atgtagcaat attagatgca ttagaagaat atcataatat gtcagaaaat    120
actgtagttg aaaagtatct aaaattaaaa gatataaaca gtttaacaga tacctatata    180
gatacatata aaaaatctgg tccaaataaa gccttaaaaa aatttaaaga gtacttagtt    240
acagagtatt agaattaaaa aatagcaatt taactccagt cgagaaaaat ttacatttta    300
tatggattgg agggcaaata aatgatactg ctattaatta tataaatcaa tggaaagatg    360
taaatagtga ctataatgtt aatgtttttt atgatagtaa tgcattttg ataaacacat     420 tgaaaaaaac tataatagaa tcagcatcaa atgatacccct tgaatcattt agagaaaatt   480
taaatgatcc tgaattaac cacactgcaa ttttcagaaa acgtatgcaa ataatctatg     540
ataaacagca aaatttcata aattactata aagctcaaaa agaagaaaat cctgaccttia   600 taattgatga tattgtaaag acatatcttt caaacgagta ttcaaaggat atagatgaac    660
ttaatgctta tattgaagag tcattaaaca aagtcacaga aaatagtgga aatgatgtta    720
gaaactttga agaattaaaa actggagaag tattcaattt atatgaacaa gagttagtag    780
aaagatggaa tcttgctggt gcatctgata tattaagagt cgctatattg aaaaatattg    840
gtggagtcta tctagatgtt gatatgttgc caggaataca cccagattta tttaaagata    900
taaataagcc tgattcagta aagacagctg tagattggga agagatgcag ttagaagcca    960
taatgaaata taagaatat ataccagaat atacttcaaa acattttgat acattggatg     1020
aagaagttca aagtagcttt gaatctgttc tagcttctaa gtctgataag tcagaaatat    1080
ttttaccact aggagatata gaggtatcac ctttagaagt aaaagttgca tttgccaaag    1140
gttctattat agatcaagct ctaatttctg caaaagactc atattgtagt gacttactaa    1200
taaaacaaat ccaaaacaga tataagatac tgaatgatac tttaggtcca attattagtc    1260
aaggtaatga ttttaatact acaatgaaca attttggtga agtttggga gctatagcta     1320 atgaagagaa tataagtttt atagcaaaaa tcggaagtta tttaagggtt ggattttatc    1380
ctgaagctaa tactacatta ctttaagtgg tcctacaata tatgcaggag cttataaaga    1440
tttattaaca tttaaagaga tgagcataga tacttctata ttgtcgatct gagttaagaa    1500
attttgaatt tcctaaggtt aatatatctc aagcaacaga acaagagaaa aatagtttat    1560
ggcaatttaa tgaagaaaga gctaaaattc aatttgaaga atacaagaaa aattattttg    1620
aaggtgcact tggagaagat gataatcttg attttctca aaatacagta actgacaaag     1680
aatatctttt agaaaagatc tcttcatcaa cgaagaagtt cagaaagagg atatgttcat    1740
tatattgttc aattacaagg agataaaatt agctatgaag cagcatgtaa cttatttgca    1800
aaaaatcctt atgacagtat actatttcaa aaaaatatag aagattcaga agtagcatat    1860
tactataatc ctacagatag tgaaatacaa gaaattgata agtatagaat tcctgataga    1920
atctctgata gacctaagat taaattgaca ctcattggtc atggcaaagc tgagtttaat    1980
actgatatat ttgcaggtct tgatgtggat tcattatctt cagaaataga aacaatatta    2040
gatttagcta aagcagatat ttctcctaaa tctatagaaa taaacttact gggatgtaac    2100
atgtttagct attctgtaaa tgtagaagag acttatcctg ggaaattatt acttagagtt    2160
aaagataaag tatcagaatt aatgccatct ataagtcaag actctattat agtaagtgca    2220
aatcaatatg aagttagaat taatagtgaa ggaagaagag aattattaga ccattctggt    2280
gaatggataa acaagaaga aagtattata aaggatattt catcaaaaga atatatatca     2340
tttaatccta agaaaataa aattatagta aaatctaaaa atttacccga attatctaca     2400
```

```
ttattacaag aaattagaaa caattctaat tcaagtgata ttgaactaga agaaaaagta    2460
atgttagcag aatgtgagat aaatgttatt tcaaatatag agacacaagt ggtagaagaa    2520
aggattgaag aagctaaaag cttaacttct gactctatta attatataaa gaatgaattt    2580
aaactaatag aatctatttc tgatgcacta tacgatttaa acaacagaa tgaattagaa     2640
gagtctcatt ttatatcttt tgaggatata tcagaagact gatgaaggct ttagtataag    2700
atttattgat aaagaaactg gagaatctat atttgtagaa actgaaaagg caatattctc    2760
tgaatatgct aatcatataa ctgaagaaat ttctaagtta aaagatacta tatttgatac    2820
tgtaaatggt aagttggtga aaaaagtaac tttagatgct acacatgaag tgaatacttt    2880
aaatgctgca ttttttatac aatcattaat tggatataat agttctaaag aatctcttag    2940
taatttaagt gtagcaatga aagttcaagt ttatgctcaa ttatttagta ctggtttaaa    3000
taccattaca gatgcggcta aagttgttga attagtatca actgcactag atgaaactat    3060
agatttactt cctacattat ctgaaggatt acctgtaatt gctactatta tagatggtgt    3120
aagtttaggt gcatcaatta aagagttgag tgaaacaagt gacccattat taagacaaga    3180
aatagaagca aaaataggta taatggcagt aaatttaaca gcagctacaa ctgcaattat    3240
tacttcatct ttaggaatag caagtggatt tagtatactt ttagttcctc tagcagggat    3300
ttcagcagga atcccaagtt tagtaaataa tgaacttata ttacgagctg aggcaaaaaa    3360
tgtcgtagat tattttggcc atatttcatt agctgaatct gaaggagcat ttactttgtt    3420
agatgataaa ataatgatgc cacaagatga tttagtaata tctgaaatag actttaataa    3480
caattcaata actttaggta aatgtgaaat atggagaatg gaaggtggtt caggtcatac    3540
tgtaaccgat gatatagatc acttcttctc agcaccatca acaacatata gggaaccata    3600
tttatctata tatgatgtat tagatgtaaa agaggaagaa cttgatttat caaaagattt    3660
aatggtatta gctaatgccc cagatagaat cttggctgg gaagaggat ggacgccagg      3720
tttaagaagc ttgaaaaatg atggtacaaa actattagac cgtataagag atcattatga    3780
agggcagttt tattggagat ttttcgcttt tatagctgat tctgtaataa caaaattaaa    3840
accaagatat gaagatacta atataagaat aagtttagac agtaatacta gaagttttat    3900
agttccagta ataactacag aatatataag agaaaaatta tcatattctt tttatggttc    3960
aggaggaact tatgcattat ctcttttctca atacaatatg aatataaaca tagaattaaa   4020
tgaaaatgat acttgggtta tagatgtcga ctaatgcgta agagatgtca ctatagaatc    4080
tgataaaatt aaaaaaggag atttaataga aaatatttta tctaaattaa gtattgaaga    4140
caataaaatt attttagata atcatgaaat taatttctct ggaacattaa atggaggtaa    4200
tggatttgta tctttaacat tctcaatctt agaaggaata aatgcagtta tagaagttga    4260
tttattatct aaatcatata agttcttat ttctggtgaa ctaaaaacat tgatggcaaa     4320
ttcaaattct gttcaacaga aaatagatta tataggattg aatagcgaat tacaaaaaaa    4380
tataccttat agttttatgg atgatgaagg aaaagaaaat ggatttatta attgttttac    4440
aaaagaaggt ttatttgtat ctgaattatc tgatgtagtt ctcataatta aagtttatat    4500
ggacaatagt aaacctccat ttggatatta gtaatgat ttgaaagatg ttaaagttat      4560
aactaaagat gacgttatta taataacagg ttaatatctt aaaagatgat ataaaaatct    4620
ctctttcttt tactatacaa gataaaaata ctataaaatt aaatggagta tatttagatg    4680
aaaatggagt agctgaaata ttgaaattta tgaataaaaa aggtagtaca aatacttcag    4740
attctttaat gagctttta gaaagtatga acataaaaag tattttcata aaatccttaa     4800
```

```
aatctaatgc taagcttata ttagatacta attttataat aagtggtact acttttattg   4860
gtcaatttga gtttatttgt gataaagata ataaatataca accatatttc attaagttta   4920
atacactaga aactaaatat actctatatg taggtaatag acaaaatatg atagtagaac   4980
caaattataa tttagatgat tctggagaca tatcttcaac tgtcattaat ttttctcaga   5040
aataccttta tggaatagac agttgtgtta ataaagttgt aatttcacca gggatttata   5100
cagatgaaat aaatataacg cctgtacatg aagcaaataa tacttatcca gaagtgattg   5160
tattagatac aaattatata agtgaaaaaa tcaatattaa tatcaatgat ttatctatac   5220
gatatgtatg gagaagtgat ggtaatgatt ttattcttat gtcaactgat gaagagaaca   5280
aggtatcaca agttaaaata agatttacta atgtttttaa aggtaatact atatcagata   5340
agatatcttt taatttagt gacaagcaag atatatctat aaataaaatt atttcaacat   5400
ttacaccttc atattatgtg aaggattac ttaattatga tttaggtctg atttctttat   5460
acaatgagaa attttatatt aataatttgg gaatgatggt gtctgggtta gtatatatta   5520
atgattcatt atattatttc aaaccaccaa taaagaactt gataactgga tttacaacta   5580
taggcgatga taaatactac tttaatccag attaatggag gacctgcttc agttggagaa   5640
acaataattg atggcaaaaa ctactatttc agccaaaatg gagtgttaca aacaggtgta   5700
tttagtacag aagatggatt taaatatttt gctccagcag atacacttga tgaaaatcta   5760
gaaggtgaag caattgattt tactggcaaa ctaattattg atgaaaatgt atattatttt   5820
ggagataatt atagagcagc tatagaatgg caaacattag atgatgaaat gtactatttt   5880
agcacagata caggtagagc ttttaaaggg ctaaatcaaa taggtgatga taaattctat   5940
ttcaactctg atggtattat gcaaaaagga tttgttaata taaatgataa gacatttat   6000 tttgatgatt ctggtgtgat gaagtcagga tatactgaaa tagatggaag atatttttac   6060
tttgctgaag atggagaaat gcaaatagga gtatttaata cagcagatgg atttaaaatat   6120 tttgctcatc atgatgaaga tttaggaaat gaagaaggtg aagcactttc atattctggt   6180
atacttaatt ttaacaataa gatttattat tttgatgatt catttacagc agtagttgga   6240
tggaaggatt tagaagatgg ttcaaaatat tactttgatg aaaatacagc agaagcatct   6300
ataggtatat caataattaa tgatgggaaa tattatttta atgattctgg aatcatgcaa   6360
attggatttg tcacaataaa taatgaagtt ttttatttct ctgattctgg aatagtagaa   6420
tctggaatgc aaaatataga tgataactat ttctatataa gtgataatgg tctagttcaa   6480
attggtgtat ttgacacttc agatggatat aaatactttg caccagctaa tactgtaaat   6540
gataatattt atggacaagc agttgaatat agtggtttag ttagagttaa tgaagatgtg   6600
tatagttttg gagaatcata tacaattgaa actggatgga tatatgattc agaaaacgaa   6660
agtgataaat attatttcga tccagaagct aaaaaagcat ataaaggtat caatgtaatt   6720
gatgatataa aatactattt tgatgagaat ggcataatga aacaggtct tataacatttt   6780 gaagataatc attactattt taatgaagat ggtgaaatgc aatatggtta tctaaatata   6840
gaagataaga tgttctactt tagtgaagat ggtattatgc agattggagt atttaataca   6900
ccagatggat ttaaatattt tgcacatcaa aatactttag atgagaattt tgagggagaa   6960 tcaataaaact atactggttg gttagattta gatgaaaaga gatattattt tacagatgaa   7020
tatatcgcag caactggttc agttattatt gatggtgagg agtattattt tgatcctgat   7080
acagctcaat tagtgattag tgaatagata a                                   7111
```

<210> SEQ ID NO 5
<211> LENGTH: 1264
<212> TYPE: DNA
<213> ORGANISM: Clostridium difficile

<400> SEQUENCE: 5

| | | | | | |
|---|---|---|---|---|---|
| tagtaatgca | tttttgataa | acacattgaa | aaaaactata | atagaatcag | catcaaatga | 60 |
| taccettgaa | tcatttagag | aaaatttaaa | tgatcctgaa | tttaaccaca | ctgcaatttt | 120 |
| cagaaaacgt | atgcaaatca | tctatgataa | acagcaaaat | ttcataaatt | actataaagt | 180 |
| tcaaaaagaa | gaaaatcacc | ttataattga | tgatattgta | agacatatc | tttcaaacga | 240 |
| gtattcaaag | gatatagatg | aacttaatgc | ttatattgaa | gagtcattaa | acaaagtcac | 300 |
| agaaaatagt | ggaaatgatg | ttagaaactt | tgaagaattt | aaaactggag | aagtattcaa | 360 |
| tttatatgaa | caagagttgg | tagaaagatg | gaatcttgct | ggtgcatctg | atatattaag | 420 |
| agtcgctata | ttgaaaaata | ttggtggagt | ctatctagat | gttgatatgt | taccaggaat | 480 |
| acacccagat | ttatttaaag | atataaataa | gcctgattca | gtaaagacag | ctgtagattg | 540 |
| ggaagagatg | cagttagaag | ccataatgaa | atataaagaa | tatataccag | aatatacttc | 600 |
| aaaacatttt | gatacattgg | atgaagaagt | tcaaagtagc | tttgaatctg | ttctagcttc | 660 |
| taagtctaat | aagtcagaaa | tatttttacc | actaggagat | atagaggtat | cacctttaga | 720 |
| agtaaaaatt | gcatttgcca | aaggttctat | tataaatcaa | gctctaattt | ctgcaaaaga | 780 |
| ctcatattgt | agtgacttac | taataaaaca | aatccaaaac | agatataaga | cactgaatga | 840 |
| tactttaggt | ccaattatta | gtcaaggtaa | tgattttaat | actacaatga | acaattttgg | 900 |
| tgaaagtttg | ggagctatag | ctaatgaaga | gaatataagt | tttatagcaa | aaatcggaag | 960 |
| ttatttaagg | gttggatttt | atcctgaagc | taatactaca | ttactttaag | tggtcctaca | 1020 |
| atatatgcag | gagcttataa | agatttatta | acatttaaag | agatgagcat | agatacttct | 1080 |
| atattgtcga | tctgagttaa | gaaatttcga | atttcctaag | gttaatatat | ctcaagcaac | 1140 |
| agaacaagag | aaaaatagtt | tatggcaatt | taacgaagaa | agagctaaaa | ttcaatttga | 1200 |
| agaatacaag | aaaaattatt | ttgaaggtgc | acttggagaa | gatgataatc | ttgattttc | 1260 |
| tcag | | | | | 1264 |

<210> SEQ ID NO 6
<211> LENGTH: 7090
<212> TYPE: DNA
<213> ORGANISM: Clostridium sordellii

<400> SEQUENCE: 6

| | | | | | |
|---|---|---|---|---|---|
| atgagcttag | ttaacaaagc | ccaattacaa | aaaatggtat | atgtaagatt | tcgtattcag | 60 |
| gaagatgagt | acgtagcaat | attaaatgct | ctagaagaat | atcacaacat | gtcagaaaat | 120 |
| agtgtagttg | aaaagtattt | aaaattaaag | gatataaata | atctcacaga | taattacctg | 180 |
| aacacatata | aaaaatctgg | aaggaataaa | gccttaaaaa | aatttaaaga | atactaacta | 240 |
| tggagtatta | gagctaaaaa | ataatagtct | aactccagtc | gaaaaaaatt | tacatttat | 300 |
| atggattgga | ggacaaataa | atgataccgc | tatcaactat | ataaatcaat | ggaaagatgt | 360 |
| aaatagcgat | tatacagtta | agtttttta | tgatagtaat | gcatttttga | taaacacatt | 420 |
| gaagaaaact | attgttgagt | cagcaacaaa | taatactctt | gagtcattta | gagaaaactt | 480 |
| aaatgacct | gaattcgatt | ataataaaat | ttatagaaaa | cgtatggaaa | taatatga | 540 |
| taaacaacaa | cattttatag | attattataa | gtctcagata | gaagagaatc | ctgacattat | 600 |

```
aattgataat attataaaaa catatctctc aaatgagtat tcaaaagacc tagatgccct    660
taataagtat attgaagaat ctttaaataa aattactgct aataatggta atgatatcag    720
aaatctagaa aaatttgctg atgaggattt ggtcagatta taatcaag  agttagtaga    780 aagatggaat ttggctgctg cttctgacat attacgaata tctatgttaa aaagatggt    840 ggtgtatatt tagatgttga catgttacca ggtatacaac cagatttatt taagatataa    900
acaagcctga ttcgataaca aatacaagtt gggaaatgat aaagttagag gccataatga    960
aatataagga atatatacca gggtatacgt caaagaattt tgacatgtta gatgaagaag   1020
ttcaacgcag ttttgaatct gctttaagtt ctaaatcaga taagtcagaa attttttgc    1080 cacttgatga tataaaagta tccccgttag aagtaaaaat tgcatttgcc aataactctg   1140
ttataaatca agccttaatt tctttaaaag attcctattg tagtgattta gtaataaatc   1200
aaattaaaaa tagatataaa atcttgaacg acaacttaaa tccatccatt aatgaaggta   1260
ctgactttaa tactacaatg aaaatttta gtgacaaatt agcatctatt tctaatgaag    1320
ataatatgat gtttatgata aaaattacaa actatttaaa agttggattt gctccagatg   1380
ttagaagtac tattaacttt aagtggacct ggagtatata caggagctta tcaagatttg   1440
ttaatgttta aagataatag tacaaatatt catttactag aacctgagtt aagaaatttt   1500
gagtttccta aaactaaaat ttctcaatta acagaacagg aaataactag tttatggtca   1560
tttaaccaag caagagccaa gtctcaattt gaagaatata aaaaaggtta ttttgaaggt   1620
gcacttggag aagatgataa tcttgatttt gctcaaaata cagtacttga taaagattat   1680
gtttctaaaa aaatattatc atcaatgaaa acccgaaata aagaatatat tcattatatt   1740
gttcaactac aaggagataa aatcagctat gaagcatcat gtaacttatt ttcaaaagaa   1800
tccttattct agtatactat atcagaaaaa tatagaaggt tcagaaacag catattacta   1860
ttatgttgca gatgctgaga taaaagaaat agataaatat agaattccat atcaaatttc   1920
taataaacgt aatattaaat taactttttat tggtcatggt aaatctgaat ttaatactga   1980
tacatttgcc aatcttgatg tagattcatt atcttctgag atagaaacaa tattaaattt   2040
agctaaagca gatatttctc ctaagtatat agaaataaat ttactgggat gtaacatgtt   2100
cagctactct atcagcgcag aagagactta tcctggaaaa ctttttactta aaattaaaga   2160 tagagtatca gaattaatgc catctataag tcaagactct attacagtaa gtgcaaatca   2220
atatgaagtt agaataaatg aagaaggaaa aagagaaata ttagatcatt ctggtaaatg   2280
gataaataaa gaagaaagta ttataaagga tatttcatca aaagaatata tatcatttaa   2340
tccaaaagaa aataaaatta tagtgaaatc taaatatttta catgagctgt ctacattatt   2400
acaagaaatt aggaataatg ccaattcaag tgatattgat ctagaaaaaa aagtaatgtt   2460
aacagaatgt gagataaatg ttgcttcaaa tatagataga cagattgtgg aaggaagaat   2520
tgaagaagct aaaaatttga cttctgactc tattaattat ataaaaaatg aatttaaact   2580
aatagaatct atttctgatt cattatatga tttaaaacat caaaatggat tagatgattc   2640
tcattttata tcttttgagg atatatccaa gactgaaaat ggatttagga taaggttcat   2700
taataaagaa actggaaact ctatatttat agaaactgaa aaagaaattt tctctgaata   2760
tgctactcat atatctaaag aaatttctaa tataaaagat actatatttg ataatgtaaa   2820
tggcaaatta gtaaaaaaag taaatctaga tgctgcacat gaagtaaaata ctctaaattc   2880 tgcctttttt atacaatcat taatcgaata taatactact aaagaatcac ttagtaattt   2940
```

```
aagtgtagca atgaaggttc aagtttatgc tcaattattt agtactggtt taaatactat    3000
tacagatgct tctaaagttg ttgagttagt atcaactgca ttagatgaaa ctatagactt    3060
acttcctaca ttatctgaag gattacctgt aattgctaca ataatagatg gtgtaagctt    3120
aggcgcggca attaaagaac tcagcgaaac aaatgaccca ttattaagac aagaaataga    3180
agccaagata ggtataatgg ctgtaaattt aacagcagct tcaactgcaa tcgttacttc    3240
agctttagga atagctagtg gttttagcat acttttagtt cctttggcag gaatttcagc    3300
agggatacca agtttagtaa acaatgaact tatactccaa gataaggcaa caaaagttat    3360
agattatttt aaacatattt cattagctga gactgaggga gcatttacat tattagatga    3420
taaaataatt atgcctcaag atgacttggt attatcagaa atagacttta ataataattc    3480
aataacttta ggtaaatgtg aaatctggag agctgaaggt ggttcaggcc ataccttaac    3540
tgatgatata gatcatttct tttcatcacc atcaataaca tatagaaaac catggttatc    3600
tatatatgat gtattaaata taaaaaaaga aaaaattgat ttttcaaaag atttaatggt    3660
attacctaat gcacctaata gggtatttgg ttatgaaatg ggatggacac cagggttcag    3720
aagtttagac aatgacggca ctaaattatt agatcgtata agagatcatt atgaaggtca    3780
attttattgg agatatttcg cttttatagc tgatgcttta ataacaaaat taaaaccacg    3840
atatgaagat actaatgtaa gaataaatct agatggcaat actagaagtt ttatagttcc    3900
agttataacc acagaacaaa taagaaaaaa tttatcttat tctttttatg gttcagggag    3960
atcttattca ttatctcttt ctccatataa tatgaatata gatttaaatc tagttgaaaa    4020
tgatacttgg gttatagatg ttgataatgt tgtaaaaaac atcactatag agtcagatga    4080
aatacaaaaa ggtgaattaa tagaaaatat tttatctaag ctaaatattg aagataataa    4140
aattatttta aataatcata ctattaattt ctatggagat ataaatgaaa gcaacagatt    4200 tatatctttta acattttcaa ttttagagga tataaatata attatagaaa ttgatttagt    4260
atcaaaatct tataaaatac ttctttctgg taattgtatg aaattgatag aaaactcatg    4320
tgtattcaac aaaagataga tcatataggg tttaatggtg aacatcagaa atatataccct    4380 tatagttata tagataatga aactaaatac aacggtttta ttgactactc taaaaaagaa    4440
ggtctgttta cagctgaatt ttctaatgaa tccattataa ggaatattta tatgcctgat    4500
agtaataatt tatttatata ttctagtaaa gatttaaaag atattagaat tataaataaa    4560
ggtgatgtta aattactaat aggaaattac tttaaagatg atatgaaggt atcacttttc    4620
ttcactatag aagatacaaa tactataaag ttgaatggtg tatatctaga tgaaaatgga    4680
gtagcacaaa tattgaaatt tatgaataat gcaaaaagtg ctttaaatac ttcaaactcg    4740
ttaatgaatt tcttagaaag tatcaacata aaaaatattt tctacaataa tctagacct    4800 aatatcgagt ttatactaga tactaatttc ataataagtg gtagcaattc tattgggcaa    4860
tttgaactta tctgtgataa agataaaaat atacaaccat attttattaa ctttaaaata    4920
aaagaaacta gctatactct atatgtagga aatagacaaa atttgatagt ggaaccaagt    4980
tatcacttag atgattctgg aaatatatct tcaactgtca ttaatttctc tcagaaatat    5040
ctttatggaa tagaccgtta tgttaataaa gttataattg caccaaattt atatacagat    5100
gaaataaata taacacctgt atataaacca aattatattt gtccagaagt tattatatta    5160
gatgcaaatt atataaacga aaaaataaat gttaatatca atgacttatc tatacgatat    5220
gtatgggata atgatggtag tgatcttatt cttatagcaa atagtgagga agataatcaa    5280
ccacaagtta aaataagatt tgttaatgtc tttaaaagcg atactgcagc agataagttg    5340
```

```
tctttaact tcagtgataa gcaagatgta tctgtaagta aaattatttc aacattttca    5400
cttgcagctt atagcgatgg attttttgac tatgaatttg gtctgtttct ttagataatg    5460
attactttta tattaatagt tttggaaata tggtatctgg attaatatat attaatgatt    5520
cattatatta tttcaaacca ccaaaaaata acttgataac tggattcaca actatagatg    5580
gtaataaata ttactttgac ccaacgaaga gtggagctgc atcaatagga gaaataacaa    5640
ttgatggtaa agattattac tttaacaaac aaggtatttt gcaagtagga gttattatta    5700
catctgatgg attaaagtat tttgctcctg ctggtacact tgatgaaaac ttagagggag    5760
atgcagtaaa ttttattgga aaattaaata ttgatgaaaa aatttattat tttgaagata    5820
attatagagc cgctgtagag tggaaattat tagatgatga acatactat ttcaatccaa     5880 aatcaggaga agcccttaaa ggtttacatc aaattggtga taataaatat tattttgatg    5940
ataatggaat tatgcaaact ggtttcatta ctataaatga taaggtattt tattttaata    6000
atgatggtgt gatgcaagtt ggatatattg aggtaaatgg taaatatttt tattttggca    6060
aaaatggaga aagacaatta ggagtattta atactccaga tggatttaaa ttttttggtc    6120
ctaaagatga tgatttagga actgaagaag gggaactaac cttatataat ggtatattga    6180
attttaatgg gaaaatctat ttttttgata tctcaaatac agctgtagtc ggatggggta    6240
ctcttgatga tggctctaca tattatttcg atgataatag agcagaagca tgcataggtt    6300
taacagtaat taatgattgt aagtattatt ttgatgataa cggataagg caattaggat     6360 ttatcactat aaatgacaat atattttatt tctctgaatc tggaaaaata gagttaggat    6420
accaaaatat aaatggtaac tatttctaca tagatgaaag tggtttagtt ctaattggag    6480
tatttgatac cccagacgga tataaatatt ttgcacctct taatactgta atgataata     6540 tttatggaca agcagttaaa tatagtggtt tagtaagggt taatgaggac gtatatagtt    6600
ttggtgaaac atataaaatt gaaactggat ggatagaaaa tgaaactgat aaatattatt    6660
ttgatccaga gactaaaaaa gcatataaag gcattaatgt agttgatgat ataaaatatt    6720
atttcgatga gaatggtata atgagaacag ggcttatatc atttgaaaat aataattatt    6780
acttcaatga agatggtaaa atgcaatttg gttatctaaa tataaaagat aaaatgtttt    6840 atttggtaa agatggtaaa atgcagattg gagtatttaa taccccagat ggatttaaat     6900
actttgcaca tcaaaatact ttagatgaga attttgaggg ggaatcaata aactatactg    6960
gttggttaga tttagatggt aaaagatatt attttacaga tgaatatata gcagcaactg    7020
gctcattgac tattgatggt tacaattact attttgaccc tgatacagct gaattagtag    7080
ttagtgaata                                                            7090
```

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
taatagaaaa cagttagaaa                                                 20

<210> SEQ ID NO 8
<211> LENGTH: 20
<212> TYPE: DNA
<213> ORGANISM: Artificial Sequence
<220> FEATURE:

```
<223> OTHER INFORMATION: oligonucleotide primer

<400> SEQUENCE: 8
tccaatccaa acaaaatgta                                              20

<210> SEQ ID NO 9
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 9
tatataaatc aatggaaaga tgtaaatagt                                    30

<210> SEQ ID NO 10
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 10
tagtaatgca tttttgataa acacattgaa a                                  31

<210> SEQ ID NO 11
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 11
tttgaaagat atgtctttac aatatc                                        26

<210> SEQ ID NO 12
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 12
ttcttcaaag tttctaacat catttccac                                     29

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 13
atatcagaga ctgatgag                                                 18

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
tagcatattc agagaatatt gt                                            22
```

```
<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
tgtagcaatg aaagtccaag tttacgc                                        27

<210> SEQ ID NO 16
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 16
ctttaaatgc tgcatttttt atacaatc                                       28

<210> SEQ ID NO 17
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 17
gaaagtccaa gtttacgctc aat                                            23

<210> SEQ ID NO 18
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 18
gctcaattat ttagtactgg tttaaatac                                      29

<210> SEQ ID NO 19
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 19
tgcacctaaa cttacaccat ctataata                                       28

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 20
gctgcaccta aacttacacc a                                              21

<210> SEQ ID NO 21
<211> LENGTH: 26
<212> TYPE: DNA
<213> ORGANISM: Artificial Sequence
<220> FEATURE:
<223> OTHER INFORMATION: oligonucleotide primer
```

-continued

```
<400> SEQUENCE: 21
cacttagctc tttgattgct gcacct                                          26

<210> SEQ ID NO 22
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 22
ctatttcttg tcttaataat gggtcac                                         27

<210> SEQ ID NO 23
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 23
gaaggtggtt caggtcatac                                                 20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
aatggaaggt ggttcaggtc                                                 20

<210> SEQ ID NO 25
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 25
cttaaacctg gtgtccatc                                                  19

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 26
cattttctaa gcttcttaaa cctg                                            24

<210> SEQ ID NO 27
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 27
ggaaaagaga atggttttat taa                                             23

<210> SEQ ID NO 28
<211> LENGTH: 23
```

```
<210> SEQ ID NO 28
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 28
acaaaagaag gtttatttgt atc                                          23

<210> SEQ ID NO 29
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 29
atctttagtt ataactttga catcttt                                      27

<210> SEQ ID NO 30
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 30
cggttgttga attagtatca actgcacaac cg                                32

<210> SEQ ID NO 31
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 31
ccggcgatgc ctcttcacat tgctccacct ttcctcgccg g                      41

<210> SEQ ID NO 32
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 32
cggttgttga attagtatca actgcacaac cg                                32

<210> SEQ ID NO 33
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 33
ccggcgatgc ctcttcacat tgctccacct ttcctcgccg g                      41
```

DETECTION OF TOXIGENIC STRAINS OF *CLOSTRIDIUM DIFFICILE*

RELATED APPLICATION

The present application is a continuation application under 35 U.S.C. §121 of U.S. patent application Ser. No. 12/203,694, filed on Sep. 3, 2008, now U.S. Pat. No. 9,096,638, which claims priority under 35 U.S.C. §119(e) to U.S. Provisional Application No. 60/970,492, filed on Sep. 6, 2007, the content of these related applications is incorporated by reference in its entirety.

FIELD OF THE INVENTION

The present invention relates to primers and probes for detection of toxin-producing (toxigenic) strains of *Clostridium difficile*, and to methods of detecting toxigenic strains using these primers and probes. More specifically, the invention relates to detection of *C. difficile* by nucleic acid-based amplification methods using particular primers and probes that bind to the toxin B (TcdB) gene. These primers and probes are used to amplify *C. difficile* nucleic acids in clinical samples to determine the presence of these toxigenic strains.

BACKGROUND OF THE INVENTION

*Clostridium difficile* is a spore-forming, gram-positive *bacillus* that produces exotoxins that are pathogenic to humans. *C. difficile*-associated disease (CDAD) ranges in severity from mild diarrhea to fulminant colitis and death. *C. difficile* typically has affected older or severely ill patients who are hospital inpatients or residents of long-term-care facilities. *C. difficile* is the major cause of pseudomembranous colitis and antibiotic associated diarrhea. *C. difficile*-associated disease occurs when the normal intestinal flora is altered, allowing *C. difficile* to flourish in the intestinal tract and produce a toxin that causes a watery diarrhea. One major cause for alteration of intestinal flora is the overuse of antibiotics. Repeated enemas, prolonged nasogastric tube insertion and gastrointestinal tract surgery also increase a person's risk of developing the disease. The overuse of antibiotics, especially penicillin (ampicillin), clindamycin and cephalosporins may also alter the normal intestinal flora and increase the risk of developing *C. difficile* diarrhea.

Toxigenic strains of *C. difficile* commonly produce two large toxins, an enterotoxin; toxin A (TcdA) and a cytotoxin; toxin B (TcdB), to which disease symptoms are attributed. They are expressed efficiently during growth of *C. difficile* in response to an environmental stimulus. Their activities modulate numerous physiological events in the cell and contribute directly to disease. In humans the two toxins cause diseases called pseudomenbranous colitis and antibiotic associated diarrhea. Transmission occurs primarily in health care facilities, where exposure to antimicrobial drugs and environmental contamination by *C. difficile* spores are common (2, 3 and 4).

Toxin A and toxin B are encoded by genes tcdA and tcdB. Both have been sequenced and are found in single open reading frames. Together with three additional genes (tcdC, tdcD, tcdE), they form a 19,6 kb chromosomal pathogenicity locus (Paloc) (8). Both open reading frames are large, with tcdA spanning 8,133 nucleotides and tcdB being 7,098 nucleotides in length. FIG. 1 shows the genetic arrangement of the *C. difficile* Paloc. tcdD, renamed tcdR (Rupnik, M. et al., J. Med. Microbiol, 2005, 54: 113-117) is a proposed positive regulator, tcdE is a putative holin protein, and tcdC is a proposed negative regulator of toxin gene expression (Voth, D. E. et al., Clinical Microbiol. Reviews, 2005, 18: 247-263).

TcdA and TcdB are among the largest bacterial toxins reported, comparable in size to lethal toxin (TcsL) and hemorrhagic toxin (TcsH) of *C. sordellii* as well as alpha toxin (Tens) of *C. novyi* (Voth, supra.). TcdA (308 kDa) and TcdB (270 kDa) are glucosyltransferases which inactivate small GTPases such as Rho, Rac and Cdc-42 within target cells (Voth, supra.). This inactivation causes disaggregation of the cellular cytoskeleton and alterations of other cellular processes which eventually lead to cell death (Voth, supra.). Both toxins use a highly conserved N-terminal domain (74% homology between TcdA and TcdB) to modify identical substrates. The proximal locations of tcdA and tcdB genes and the high sequence and functional homology between the two proteins inspired Von Eichel-Streiber to propose that the two genes may have arisen as the result of gene duplication (Knoop F. C. et al, Clin. Micro reviews, July 1993, 251-265).

TcdB also exhibits homology (85% homology and 74% identity) with lethal toxin (TscL) of *C. sordellii*, which glycosylates Ras, Rac, Rap and Ral. The major differences are found in the N terminus. These explain the differences in substrate specificity. TcdA is thought to be more similar in function to the hemorrhagic toxin (TcsH) of *C. sordellii* (Voth, supra.).

In early studies, it had been generally accepted that *C. difficile* toxigenic strains produced both toxin A and toxin B whereas nontoxigenic strains lacked both toxins (Rupnik et al. supra.; Lyerly et al., Clin. Micro. Rev., 1998, Jan., 1-18). Toxin variant strains were then discovered which failed to produce detectable toxin A, and yet produced toxin B (TcdA−/TcdB+). A third toxin (binary toxin CDT) has also been found in some *C. difficile* strains. Although the majority of binary toxin positive strains produce TcdA and TcdB (TcdA+TcdB+CDT+) some produce neither TcdA nor TcdB (TcdA-TcdB-CDT+). In the light of available data, *C. difficile* strains into toxigenic strains were classified as toxigenic if they produced at least one of the three known toxins, and nontoxigenic strains if they did not produce any of these three toxins (Rupnik et al., supra.).

While the primary work on TcdA and TcdB was carried out on toxins from the toxigenic reference strain VP1 10463, several genetic variants of these toxins now exist in clinical isolates (Voth et al., supra.). Two well-characterized strains which do not express toxin A (TcdA−/TcdB+), 1470 and 8864, produce modified toxin B compared to VP1 10463. Strain 1470 produces a hybrid of toxins TcdB and TcsL. The strain produces TcdB-like cell contact and a TcsL-like enzymatic domain (morphological change and cell death like TcsL) (Voth, supra.; Chaves-Olarte E. et al, The Journal of biological chemistry, 1999, 274, no 16, 11046-11052). As mentioned above, toxin B from reference strain 10463 inactivated small GTPases as Rho, Rac and Cdc-42. The impact is visible on electron microscopy with a modification of cellular aspect. Two types of cytopathic effects are described. The D-type is characterized by an arborized appearance of the cells whereas a spindle-like appearance is typical of the second type of cytopathic effect, the S-type (Mehlig, et al., FEMS Microbiol. Lett., 2001, 198:171-176). Toxin B of reference strain show D-type cytopathic effect as well as toxin A. Strains with lack of toxin A production, such as strain 1470 and strain 8864, produce toxin B with S-type cytopathic effect. Substrates for these toxins B are small GTPases Ras, Rac, Rap, Ral and Cdc-42. Both strains show variations in their toxin B gene (tcdB) compared to VP1

14063 tcdB gene. These variations explain the differences in substrate specificity. A difference in the N-terminal region of the tcdB of 1470 strain and VP1 10463 has been well documented (Von Eichel-Streiber et al, Mol Microbiol, 1995, 17: 313-321).

Another toxin B variant strain was discovered that produces functional toxin A. Thus, strain C34 is the first *C. difficile* strain that expresses a variant toxin B as 1470 and 8864, and a functional toxin A as reference type strain 14063 (Mehlig et al., supra.). This strain produces a toxin B with S-type cytopathic effect such as strain 1470 and 8864. C34 is the first *C. difficile* isolate coexpressing a D-type-inducing TcdA with an S-type-inducing TcdB molecule. The substrates of TcdA-C34 and the reference strain TcdA-10463 are identical (Rho, Rac and Cdc-42), and the substrates of TcdB-C34 and TcdA-1470 or 8864 are identical (Ras, Rac, Rap, Ral and Cdc-42). The tcdB sequence from C34 differs only in nucleotides from tcdB-1470 or 8864. Instead of having a deletion in tcdA that prevents toxin A production as strains 1470 and 8864, there is an inserted sequence in tcdA-C34. This small insertion does not have a negative effect on toxin A production. Nevertheless, in this strain, the S-type cytopathic effect on cells dominates over the D-type cytopathic effect (Mehlig et al., supra.).

To date, one variant strain has been described that produces a generally intact tcdB but a non-functional toxin B lacking a cytotoxic effect, and a functional toxin A having a cytotoxic effect. Toxinotyping data of this variant showed limited mutation in the Paloc and classified this strain in toxinotype IX (TcdA+/TcdB+/CDT+) (abstract, Maccannell et al, 2006). Recently, outbreaks of hypertoxigenic *C. difficile* strains have been reported in Canada and the United States. These isolates were positive for CDT binary toxin, had a deletion in the tcdC gene and produced greater amounts of toxins A and B (McDonald et al, New Engl. J. Med., December 2005, 353, no 23). The emergence of similar *C. difficile* isolates in the UK, Belgium and the Netherlands has also been described. The epidemic strain isolated in those countries was characterized as toxinotype III, North American PGEF 1 (NAP1), restriction endonuclease analysis group type B1 and PCR ribotype 027 (Kuijper E et al, document for European Centre for Disease prevention and Control, *Emergence of Clostridium difficile-associated disease in Canada, the United State of America and Europe*).

For *C. difficile* toxigenic strains, nucleotide sequence variations, deletions and duplications in the Paloc (tcdB and tcdA region) account for various types. A typing system has been developed which distinguishes the various types and classifies them as toxinotypes (1, 8, 9, 10, 11, 12, 13, 19). Toxinotyping involves detection of polymorphisms in the pathogenicity locus (Paloc) precisely in the tcdA and tcdB genes. There are now at least 24 toxinotypes (See Table 1). Strains in which the Paloc is identical to the reference strain VP1 10463 are referred as toxinotype 0. Not all variations of toxin genes affect toxin production. Strains of toxinotypes IX, XII-XV and XVIII-XXIV produce both toxins A and B despite variations in their toxin genes (8, 11, 13, 19). Strains of toxinotype XI do not produce toxin A or B (13) whereas strains of toxinotypes VIII, X, XVI and XVII produce a functional toxin B but no toxin A (13). FIG. 2 describes well the relation between toxinotype and toxin expression. Strain 1470 belongs to toxinotype VIII and strain 8864 to toxinotype X. Most of the TcdA-/TcdB+ strains are known to belong to toxinotype VIII and produce a variant toxin B like strain 1470 while toxinotype X contains only strain 8864 (11).

TABLE 1

*Clostridium difficile* toxinotypes

| Toxinotype | Strain | Strain origin | Toxin, production([1]) |
|---|---|---|---|
| 0 | VP1 10463 | USA | A+B+ CDT− |
| I | EX623 | Belgium | A+B+ CDT− |
| II | AC008 | France | A+B+ CDT− |
| IIIa | SE884 | Not available | A+B+ CDT+ |
| IIIb | R10278 | Not available | A+B+ CDT+ |
| IIIc | CH6230 | Not available | A+B+ CDT+ |
| IV | 55767 | Belgium | A+B+ CDT+ |
| V | SE881 | France | A+B+ CDT+ |
| VI | 51377 | Belgium | A+B+ CDT+ |
| VII | 57267 | Belgium | A+B+ CDT+ |
| VIII | 1470 | Belgium | A−B+ CDT− |
| IX | 51680 | Belgium | A+B+ CDT+ |
| X | 8864 | England | A−B+ CDT+ |
| XI a | IS58 | Not available | A−B− CDT+ |
| XI b | R11402 | Not available | A−B− CDT+ |
| XII | IS25 | Not available | A+B+ CDT− |
| XIII | R9367 | Not available | A+B+ CDT− |
| XIV | R10870 | England | A+B+ CDT+ |
| XV | R9385 | Not available | A+B+ CDT+ |
| XVI | SUC36 | Indonesia | A−B+ CDT+ |
| XVII | J9965 | Japan | A−B+ CDT+ |
| XVIII | GAI00166 | Korean | A+B+ CDT− |
| XIX | TR13 | Japan | A+B+ CDT− |
| XX | TR14 | Japan | A+B+ CDT− |
| XXI | CH6223 | USA | A+B+ CDT− |
| XXII | CH6143 | USA | A+B+ CDT− |
| XXIII | 8785 | Belgium | A+B+ CDT+ |
| XXIV | 597B | Kuwait | A+B+ CDT+ |

[1]A+ and B+ refers to production of toxin TcdA and TcdB; CDT+ refers to the presence of complete CDT locus.

The consensus sequence for the tcdB gene was determined using 6 available sequences in GenBank (See Appendix I). The first and seventh sequences in the tcdB alignment (SEQ ID NO: 1) are the reference strain VP1 14063 TcdA+/TcdB+. The second and third sequences in Appendix I (SEQ ID NOS 2 and 3, respectively) are two well-characterized TcdA−/TcdB+ strains (1470, second line and strain 8864, third line). The fourth line is another TcdA−/TcdB+ strain (5340) (SEQ ID NO: 4). The variant toxB and functional toxA strain C34 cluster 1-2 sequence (SEQ ID NO: 5) is shown in the fifth line, and the *C. sordellii* lethal toxin (TcsL) sequence (SEQ ID NO: 6) is shown in the sixth line as a specificity control. SEQ ID NO: 5 ends at nucleotide 1695. Thus, the six sequences in the alignment from nucleotides 1696 to 7095 (top to bottom) are SEQ ID NOS: 1, 2, 3, 4, 6, and 1, respectively. From nucleotides 7096 until the end of the sequence, SEQ ID NO: 1 is only shown once (top sequence), with the remaining sequences (top to bottom) being SEQ ID NOS: 1, 2, 3, 4, and 6, respectively. Certain regions of the tcdB gene are conserved among these different strains.

A positive culture for *C. difficile* without a toxin assay is not sufficient to make the diagnosis of *C. difficile*-associated disease. Thus, toxigenic *C. difficile* detection by a tissue culture cytotoxin assay is often considered the "gold standard." However, this assay is time consuming, as it implies an incubation period of at least 24 h. The present invention provides a real-time PCR assay targeting the *C. difficile* toxin gene tcdB that is rapid, sensitive, and specific, and allows detection of *C. difficile* directly from clinical samples, such stool samples.

SUMMARY OF THE INVENTION

The present invention provides primers and probes for detection of toxin-producing (toxigenic) strains of *C. dif-*

*ficile*. These primers and probes are shown in Tables 2-4, and methods of detecting toxigenic strains of *C. difficile* using these probes and primers.

One embodiment of the present invention is an oligonucleotide probe or primer up to about 100 nucleobases in length which is capable of hybridizing to a *C. difficile* toxin B (TcdB) gene, wherein said probe or primer comprises a sequence selected from the group consisting of SEQ ID NO: 1-33, or a sequence that exhibits at least about 85% identity to a sequence selected from the group consisting of SEQ ID NOS: 1-33. In one embodiment, the probe or primer has a sequence selected from the group consisting of SEQ ID NO: 1-33, or a sequence that exhibits at least about 85% identity to a sequence selected from the group consisting of SEQ ID NOS: 1-33. In another embodiment, the probe or primer has a sequence selected from the group consisting of SEQ ID NOS: 1-33. The present invention also provides a method for detecting the presence of a toxigenic strains of *C. difficile* in a biological sample, comprising contacting the sample with at least one pair of primers capable of binding to a *C. difficile* toxin B (TcdB) gene, in which each primer in the at least one pair of primers is up to about 100 nucleobases in length, and is capable of binding to a *C. difficile* toxin B (TcdB) gene, and in which each primer in the at least one pair of primers comprises a sequence shown in SEQ ID NOS: 1-33, or a sequence that exhibits at least about 85% identity to a sequence shown in SEQ ID NOS: 1-33; amplifying target nucleic acid from the sample; and detecting the presence or amount of an amplified product(s) as an indication of the presence of the toxigenic strain of *C. difficile* in said sample.

In one embodiment, the sample is a stool, sputum, peripheral blood, plasma, serum, lymph node, respiratory tissue or exudate sample. In another embodiment, the sample is contacted with one pair of primers. In yet another embodiment, the amplifying is carried out with polymerase chain reaction (PCR), ligase chain reaction (LCR), strand displacement amplification (SDA), replicase-mediated amplification or transcription-mediated amplification. Preferably, the amplifying is carried out using PCR. Types of PCR include AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR. In one embodiment, the PCT is quantitative real-time PCT (QRT-PCR). In another embodiment, each primer introduces exogenous nucleotide sequence which allows post-amplification manipulation of amplification products without a significant effect on amplification itself. In certain embodiments, the primer pair comprises SEQ ID NOS: 30 and 31 or 31 and 32. In one embodiment, each primer in the primer pair is flanked by complementary sequences comprising a fluorophore at the 5' end, and a fluorescence quencher at the 3' end.

DETAILED DESCRIPTION OF THE PREFERRED EMBODIMENT

Figure 1:
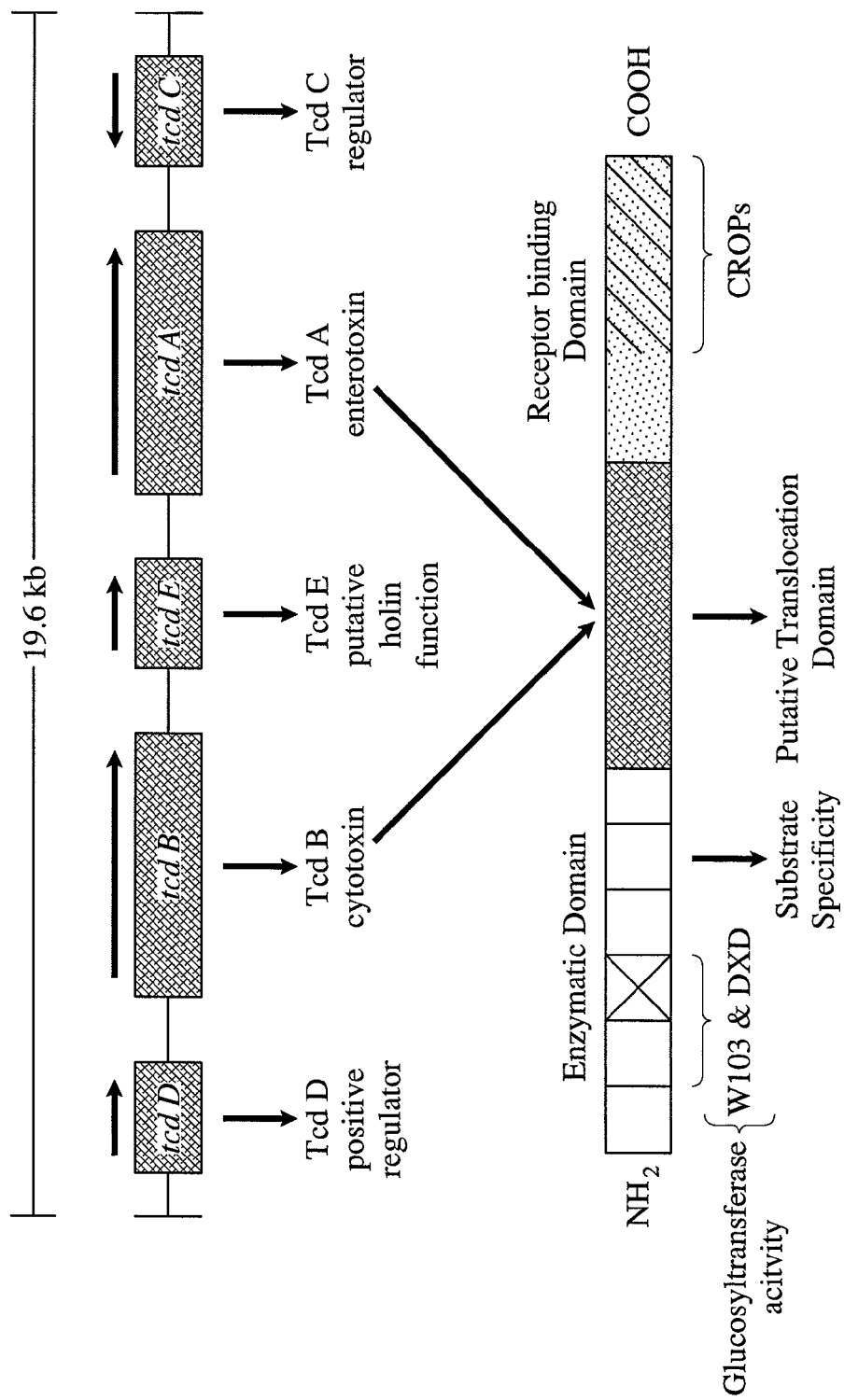
FIG. 1 shows the genetic arrangement of the *C. difficile* pathogenicity locus and proposed protein domain structure of the TcdA and TcdB genes.

The present invention relates to the detection of toxigenic strains of *Clostridium difficile* using particular primers and probes that bind to the toxin B (TcdB) gene of *C. difficile*. These primers and probes are used to amplify *C. difficile* nucleic acids in clinical samples to determine the presence of toxogenic strains.

As used herein, "template" refers to all or part of a polynucleotide containing at least one target nucleotide sequence.

As used herein, a "target nucleotide sequence" includes the nucleotide sequence of the final product having defined sequence and length, and may include other nucleotide sequences that are removed during post-amplification processing of the amplification product. Nucleotide sequences that are found in the target nucleotide sequence and later removed may include binding sites (annealing sites) for primers or probes, nucleotides involved in conversion of double-stranded DNA to single-stranded DNA, or sequences useful as recognition and/or cleavage sites for restriction endonucleases.

An "exogenous nucleotide sequence" as used herein, refers to a sequence introduced by primers or probes used for amplification, such that amplification products will contain exogenous nucleotide sequence and target nucleotide sequence in an arrangement not found in the original template from which the target nucleotide sequence was copied.

The template may be any polynucleotide suitable for amplification, where the template contains at least one target nucleotide sequence to be amplified. Suitable templates include DNA and RNA molecules, and may include polynucleotides having modified bases. Preferably, templates are genomic DNA, cDNA, or RNA molecules. In another preferred embodiment, methods disclosed herein can be used to amplify RNA templates directly, without reverse-transcribing the RNA template into cDNA.

By "clinical sample" is meant any tissue or material derived which may contain *C. difficile* nucleic acid, including, for example, stools (liquid or soft), sputum, peripheral blood, plasma, serum, biopsy tissue including lymph nodes, respiratory tissue or exudates, or other body fluids, tissues or materials. The sample may be treated to physically, chemically and/or mechanically disrupt tissue or cell structure, thus releasing intracellular components. Sample preparation may use a solution that contains buffers, salts, detergents and the like which are used to prepare the sample for analysis.

By "nucleic acid" is meant a polymeric compound comprising nucleosides or nucleoside analogs which have nitrogenous heterocyclic bases, or base analogs, linked together by nucleic acid backbone linkages (e.g., phosphodiester bonds) to form a polynucleotide. Conventional RNA and DNA are included in the term "nucleic acid" as are analogs thereof. The nucleic acid backbone may include a variety of linkages, for example, one or more of sugar-phosphodiester linkages, peptide-nucleic acid bonds, phosphorothioate or methylphosphonate linkages or mixtures of such linkages in a single oligonucleotide. Sugar moieties in the nucleic acid may be either ribose or deoxyribose, or similar compounds with known substitutions. Conventional nitrogenous bases (A, G, C, T, U), known base analogs (e.g., inosine), derivatives of purine or pyrimidine bases and "abasic" residues (i.e., no nitrogenous base for one or more backbone positions) are included in the term nucleic acid. That is, a nucleic acid may comprise only conventional sugars, bases and linkages found in RNA and DNA, or may include both conventional components and substitutions (e.g., conventional bases and analogs linked via a methoxy backbone, or conventional bases and one or more base analogs linked via an RNA or DNA backbone).

"Primer" means an oligonucleotide sequence that is designed to hybridize with a complementary portion of a target sequence, a probe, or a ligation product, and undergo primer extension. A primer functions as the starting point for the polymerization of nucleotides (Concise Dictionary of Biomedicine and Molecular Biology, (1996) CPL Scientific Publishing Services, CRC Press, Newbury, UK). A primer generally contains about sixteen to twenty-four nucleotides, but may contain up to about 50, 75 or 100 nucleotides. Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

The term "primer extension" means the process of elongating a primer that is annealed to a target in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand.

By "probe" is meant a nucleic acid oligomer that hybridizes specifically to a target sequence in a nucleic acid, under conditions that allow hybridization, thereby allowing detection of the target or amplified nucleic acid. The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe. Sequences are "sufficiently complementary" if they allow stable hybridization in appropriate hybridization conditions of a probe oligomer to a target sequence that is not completely complementary to the probe's target-specific sequence.

By "sufficiently complementary" is meant a contiguous nucleic acid base sequence that is capable of hybridizing to another base sequence by hydrogen bonding between a series of complementary bases. Complementary base sequences may be complementary at each position in the oligomer sequence by using standard base pairing (e.g., G:C, A:T or A:U) or may contain one or more residues that are not complementary (including abasic positions), but in which the entire complementary base sequence is capable of specifically hybridizing with another base sequence in appropriate hybridization conditions. Contiguous bases are preferably at least about 80%, more preferably at least about 90%, and most preferably 100% complementary to a sequence to which an oligomer is intended to hybridize.

Those skilled in the art can readily choose appropriate hybridization conditions which can be predicted based on base sequence composition, or be determined by using routine testing (e.g., see Sambrook et al., Molecular Cloning, A Laboratory Manual, 2.sup.nd ed. (Cold Spring Harbor Laboratory Press, Cold Spring Harbor, N.Y., 1989).

The terms "duplex" means an intermolecular or intramolecular double-stranded portion of a nucleic acid which is base-paired through Watson-Crick, Hoogsteen, or other sequence-specific interactions of nucleobases. A duplex may consist of a primer and a template strand, or a probe and a target strand. A "hybrid" means a duplex, triplex, or other base-paired complex of nucleic acids interacting by base-specific interactions, e.g. hydrogen bonds.

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

In accordance with one aspect of the present invention, primers and/or probes are utilized to permit amplification of a *C. difficile* nucleic acid template containing a tcdB-derived target nucleotide sequence and to optionally introduce additional features into the amplification products. Each primer and/or probe contains a nucleotide sequence that is complementary to a region of target nucleotide sequence in the template, in order for each primer to bind (anneal) to the template. In one embodiment, at least one primer contains exogenous nucleotide sequence 5' (upstream) of the primer sequence complementary to the primer-binding target nucleotide sequence, with the result that each amplification product contains exogenous nucleotide sequence introduced by the primer.

Primers and/or probes having up to about 100 nucleotides comprising any of the primer and/or probe sequences described herein, and the use of these primers to detect the presence of the *C. difficile* TcdB gene in clinical samples using nucleic acid amplification-based methods (e.g., PCR), are also within the scope of the present invention. In addition, primers and/or probes that exhibit about 70%, 75%, 80%, 85%, 90%, 91%, 92%, 93%, 94%, 95%, 96%, 97%, 98% or 99% nucleic acid identity to any of the specific primers and/or probes described herein, and the use of these primers to detect the presence of the *C. difficile* TcdB gene in clinical samples using nucleic acid amplification-based methods, are also contemplated, as are primers and/or probes having up to about 100 nucleotides comprising any of these homologous sequences.

In another embodiment, two primers are used, where each primer introduces exogenous nucleotide sequence that allow post-amplification manipulation of amplification products without a significant effect on amplification itself. Alternately, more than two primers are used, where each primer introduces exogenous nucleotide sequence that allow post-amplification manipulation of amplification products without a significant effect on amplification itself. Primers for a particular embodiment may be designed by one of skill in the art according to well-known principles, for example as disclosed in Dieffenbach and Dveksler ("General Concepts For PCR Primer Design" in, PCR Primer: A Laboratory Manual, Dieffenbach and Dveksler, eds.)

Nucleic acid amplification refers to any known procedure for obtaining multiple copies of a target nucleic acid sequence or its complement or fragments thereof, using sequence-specific methods. Known amplification methods include, for example, Polymerase Chain Reaction (PCR), Ligase Chain Reaction (LCR), Strand Displacement Amplification (SDA), replicase-mediated amplification and transcription-mediated amplification.

PCR refers to a method well-known in the art for amplification of nucleic acid. PCR involves amplification of a target sequence using two or more extendable sequence-specific oligonucleotide primers that flank the target sequence. The nucleic acid containing the target sequence of interest is subjected to a precise program of multiple rounds of thermal cycling (denaturation, annealing and extension) in the presence of the primers, a thermostable DNA polymerase (e.g., Taq polymerase) and the four dNTPs, resulting in amplification of the target sequence. PCR uses multiple rounds of primer extension reactions in which complementary strands of a defined region of a DNA molecule are simultaneously synthesized by a thermostable DNA polymerase. At the end of each cycle, each newly synthesized DNA molecule acts as a template for the next cycle. During repeated rounds of these reactions, the number of newly synthesized DNA strands increases exponentially such that after 20 to 30 reaction cycles, the initial template DNA will have been replicated several thousand-fold or million-fold. Methods for carrying out different types and modes of PCR are thoroughly described in the literature, for example in "PCR Primer: A Laboratory Manual" Dieffenbach and Dveksler, eds. Cold Spring Harbor Laboratory Press, 1995, and by Mullis et al. in patents (e.g., U.S. Pat. Nos. 4,683,195, 4,683,202 and 4,800,159) and scientific publications (e.g. Mullis et al. 1987, Methods in Enzymology, 155:335-350) where the contents of each reference are hereby incorporated by reference in their entireties.

PCR generates double-stranded amplification products suitable for post-amplification processing. If desired, amplification products can be detected by visualization with agarose gel electrophoresis, by an enzyme immunoassay format using probe-based colorimetric detection, by fluorescence emission technology, or by other detection means known to one of skill in the art.

Methods for a wide variety of PCR applications are widely known in the art, and are described in many sources, for example, Ausubel et al. (eds.), Current Protocols in Molecular Biology, Section 15, John Wiley & Sons, Inc., New York (1994). Variations of PCR include AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELIS A, PCR-RFLP, PCR-single strand conformation polymorphism (PCR-SSCP), quantitative competitive PCR (QC-PCR), rapid amplification of cDNA ends-PCR (RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR. These techniques are described, for example, at www.perlinks.com.

Real-time polymerase chain reaction, also called quantitative real time polymerase chain reaction (QRT-PCR), is used to simultaneously quantify and amplify a specific part of a given DNA molecule. It is used to determine whether a specific sequence is present in the sample; and if it is present, the number of copies of the sequence that are present. The term "real-time" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with fluorescence resonance energy transfer (FRET) probes measures fluorescent dye signal changes from cycle-to-cycle, preferably minus any internal control signals. The real-time procedure follows the general pattern of PCR, but the DNA is quantified after each round of amplification. Two common methods of quantification are the use of fluorescent dyes (e.g., Sybr Green) that intercalate into double-stranded DNA, and modified DNA oligonucleotide probes that fluoresce when hybridized with a complementary DNA.

LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.).

In strand displacement amplification, a double-stranded DNA target is denatured and hybridized with two primers, or the primers invade the DNA helix. The two primers contain an internal sequence for enzyme nicks to be placed in the newly formed DNA helix. The thermal stable DNA polymerase lacking a 5'→3' exonuclease activity, extends both primers. Generation of single stranded nicks creates new DNA extension sites and the hybridization of the first primer creates additional DNA extension sites for exponential DNA amplification.

Certain Embodiments of the invention include the following primers and probes (either RNA or DNA), that bind to the TcdB gene of *C. difficile*.

Design and Molecular Characterization of Probes and Primers

The design of primers and probes in any PCR diagnostic assay is always a compromise between sensitivity and specificity, and involves consideration of rapidity and hybridization temperature. The shortest amplicon is generally designed in order to maximize its accumulation and reduce the cycling time. The temperature difference between the melting temperature of the primers and the molecular beacon probe (defined below) is generally as high as possible. This can be achieved by varying the length and GC content of beacon stems. Such optimization of primers and probes requires a certain amount of theoretical data, obtained from database analysis and computations on nucleic acid sequences. A brief summary of relevant data is provided below.

Primers were designed using sequence databases and the software Oligo™ (version 6.0; National Biosciences). Primer design was based on melting temperature, GC content, the length of the amplicon, the ability to form as few hairpin structures as possible, their ability to form as few inter-secondary structures as possible with another primer molecule of the same sequence (homodimers), their ability to form as few inter-secondary structures as possible with other primers and probes (heterodimers), and their specificity for the toxB DNA gene sequence. Tm and GC % calculations were done using the Integrated DNA Technology (IDT) OligoAnalyzer 3.0 program, available on the IDT website (scitools.idtdna.com/Analyzer/oligocalc.asp). Parameters used were 0.25 µM for all primers, 100 mM Na+ and DNA as target. To allow an overview of the primers of the BD GeneOhm™ Cdiff assay, the primers used to amplify the target are described in Table 2.

TABLE 2

| NAME | SEQUENCE (5'-3') | POSITION | SEQ ID: |
|---|---|---|---|
| (1) VJ-tcdB-F | TAATAGAAAACAGTTAGAAA | 12-31 | 7 |
| VJ-tcdB-R | TCCAATCCAAACAAAATGTA | 312-293 | 8 |
| (2) NP1-tcdB-F2 | TATATAAATCAATGGAAAGATGTAAATAGT | 340-369 | 9 |
| NP1-tcdB-F1 | TAGTAATGCATTTTTGATAAACACATTGAAA | 396-426 | 10 |
| NP1-tcdB-R2 | TTTGAAAGATATGTCTTTACAATATC | 635-610 | 11 |
| NP1-tcdB-R1 | TTCTTCAAAGTTTCTAACATCATTTCCAC | 745-707 | 12 |
| (3) tcdB-2667 (MGB-tcdB-F) | ATATCAGAGACTGATGAG | 2665-2682 | 13 |
| tcdB-2746 (MGB-tcdB-R) | TAGCATATTCAGAGAATATTGT | 2767-2746 | 14 |
| (4) NK-104 (NK-tcdB-F) | GTGTAGCAATGAAAGTCCAAGTTTACGC | 2945-2972 | 15 |
| KERLA-tcdB-2873-F1 | CTTTAAATGCTGCATTTTTTATACAATC | 2873-2900 | 16 |
| KE-tcdB-F | GAAAGTCCAAGTTTACGCTCAAT | 2955-2977 | 17 |
| KENP-tcdB-F1 | GCTCAATTATTTAGTACTGGTTTAAATAC | 2971-2999 | 18 |
| KENP-tcdB-3102-R1 | TGCACCTAAACTTACACCATCTATAATA | 3129-3102 | 19 |
| KE-tcdB-R | GCTGCACCTAAACTTACACCA | 3131-3111 | 20 |
| NK-105 (NK-tcdB-R) | CACTTAGCTCTTTGATTGCTGCACCT | 3148-3123- | 21 |
| NKMER-tcdB-R3 | CTATTTCTTGTCTTAATAATGGGTCAC | 3181-3155 | 22 |
| (5) SP-tcdB-F | GAAGGTGGTTCAGGTCATAC | 3517-3536 | 23 |
| EF-tcdB-F1 | AATGGAAGGTGGTTCAGGTC | 3513-3542 | 24 |
| EF-tcdB-R1 | CTTAAACCTGGTGTCCATC | 3722-3704 | 25 |
| SP-tcdB-R | CATTTTCTAAGCTTCTTAAACCTG | 3736-3713 | 26 |
| (6) JLP-tcdB-F | GGAAAAGAGAATGGTTTTATTAA | 4405-4427 | 27 |
| JLPNP-tcdB-F | ACAAAAGAAGGTTTATTTGTATC | 4435-4457 | 28 |
| JLP-tcdB-R | ATCTTTAGTTATAACTTTGACATCTTT | 4566-4540 | 29 |

F = FORWARD; R = REVERSE

Primers KERLA-tcdB-2873 and KENP-tcdB-3102 were designed for *Clostridium difficile* toxin B gene amplification. Their characteristics are shown in Table 3. This simplex allows the amplification of the target. This primer set was chosen because both have similar GC contents and melting temperatures ($T_m$). Furthermore, the amplicon generated with these primers is 257 bp long for the toxin B gene target, which is suitable for a real-time PCR assay using molecular beacon probes. The primers KERLA-tcdB-2873 and KENP-tcdB-3102 also serve as primers for the internal control pDIFFa.

TABLE 3

| Primer | Sequence | Tm (° C.) | Length (bp) | GC % | Orientation | Amplicon size (bp) |
|---|---|---|---|---|---|---|
| KERLA-tcdB-2873 | 5'CTTTAAATGCTGCATTTTTTATACAATC 3' (SEQ ID NO: 30) | 56.8 | 28 | 25.0 | Forward | 257 |

TABLE 3-continued

| Primer | Sequence | Tm (° C.) | Length (bp) | GC % | Orientation | Amplicon size (bp) |
|---|---|---|---|---|---|---|
| KENP-tcdB-3102 | 5'TGCACCTAAACTTACACCATCTATAATA 3' (SEQ ID NO: 31) | 59.6 | 28 | 32.1 | Reverse | |

Molecular beacons are single-stranded oligonucleotide hybridization probes that form a stem-and-loop structure. The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo a conformational change that enables them to fluoresce brightly.

In the absence of targets, the probe is dark, because the stem places the fluorophore so close to the nonfluorescent quencher that they transiently share electrons, eliminating the ability of the fluorophore to fluoresce. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, restoring fluorescence.

Molecular beacons can be used as amplicon detector probes in diagnostic assays. Because nonhybridized molecular beacons are dark, it is not necessary to isolate the probe-target hybrids to determine the number of amplicons synthesized during an assay. Molecular beacons are added to the assay mixture before carrying out gene amplification and fluorescence is measured in real time. The assay tube remains sealed. Consequently, the amplicons cannot escape to contaminate untested samples. Furthermore, the use of molecular beacons provides an additional level of specificity. Because it is very unlikely that false amplicons or primer-dimers possess target sequences for the molecular beacons, the generation of fluorescence is exclusively due to the synthesis of the intended amplicons.

Molecular Beacon Design

Molecular beacons were designed to target the tcdB sequence and the internal control pDIFFa Using sequence databases and the software Oligo™ (version 6.0; National Biosciences). The different criteria taken into consideration when selecting molecular beacon probes are summarized below Contain conserved sequence only from species to detect (or from species characteristics to detect), and shows the required specificity.
Probe length ~20 to 30 nucleotides.
Probe does not hybridize on parts of the amplified target showing secondary structures.
Required Tm according to the assay.
GC content of 60% to 80%
Only one structure (hairpin loop) at both synthesis and annealing temperatures.
Delta G at annealing temperature <0.
No mismatches between probe and appropriate target.
Temperature difference between the Tm of the primers and the molecular beacon as high as possible.
Sequence alignments do not demonstrate cross reactivity between probes nor between probes and primers.

Molecular Beacons NK-toxB-B34-A0 and Sign-B4-B0 (Table 4) were chosen because their characteristics correspond to the best compromise between all established theoretical criteria. The Sign-B4-B0 probe hybridizes with the forward strand of the internal control amplicons, while NK-toxB-B34-A0 hybridizes with the reverse strand of the C. difficile toxin B gene. For detection of toxin B gene amplicons, the molecular beacon NK-toxB-B34-A0 bears the fluorophore 5'-carboxyfluorescein (FAM) at its 5' end and the nonfluorescent quencher moiety dabcyl chloride (DABCYL) at its 3' end. For detection of the IC amplicons, the molecular beacon Sign-B4-B0 includes the fluorophore tetrachlorofluorescein (TET) at its 5' end, and the nonfluorescent quencher moiety DABCYL at its 3' end. The NK-toxB-B34-A0 probe provides the positive signal in the assay and Sign-B4-B0 determines the validity of the PCR reaction in the assay. Their characteristics are shown in Table 4.

TABLE 4

| Probe | Target | Fluorophore | Size (nucleotides) | GC % | Sequence * |
|---|---|---|---|---|---|
| NK-toxB-B34-A0 | tcdB | FAM | 32 | 43.8 | 5' cgGTTGTTGAATTAGTATCAACTGCAcaaccg 3' (SEQ ID NO: 32) |
| Sign-B4-B0 | pDIFFa | TET | 41 | 63 | 5' ccggcGATGCCTCTTCACATTGCTCCACCTTTCC Tcgccgg 3' (SEQ ID NO: 33) |

* The stem sequences are in small letters as the hybridizing sequences are in capital letters. Some nucleotides from the hybridizing sequence can also be part of the stem sequence and are thus underlined.

Formation of Hairpin Structures

The proper design of an assay also involves the verification of potential problems for the amplification reaction. The amplification efficiency can be greatly affected by secondary structures and mismatches between primers, probes and their respective targets. To prevent such occurrences, the ability of all primers to form hairpin structures was evaluated with IDT OligoAnalyzer 3.0 software available on IDT's website. Parameters used were 0.25 μM of each primer, 100 mM Na$^+$, 5.5 mM MgCl$_2$, target DNA, hybridization temperature of 57° C. Since the hybridization depends on the thermodynamic characteristics of the molecules involved, secondary structures or undesired matches can thus be predicted and avoided. In addition, in all reactions in a PCR assay occurring in solution, the Gibbs free energy (noted ΔG and expressed in kcal/mol) is predictive of whether or not a match is likely to occur. ΔG negative values are indicative of the formation of a proposed structure or match, whereas positive values of ΔG indicate that a proposed structure is thermodynamically unstable and a match is unlikely to occur. Two hairpin structures can be formed with primer KERLA-tcdB-2873 (ΔG=0.86 and 0.89 kcal/mol), and two hairpin structures can be formed with primer KENP-tcdB-3012 (ΔG=1.9 and 2.35 kcal/mol). These structures are all thermodynamically unstable (positive ΔG).

goAnalyzer 3.0 software available on IDT's website. Parameters used for the analysis were 0.25 μM of each primer, 100 mM Na$^+$ and DNA as target. Homoduplexes of primers involving less than 7 consecutive base pairs corresponding to 25% of the total sequence (28 bp length) are very unlikely to form. Two structures formed with KERLA-tcdB-2873 involve 6 consecutive bases corresponding to 21% of the size of the primer. This is not enough to generate a stable duplex (Table 5). With KENP-tcdB-3102, hybridizations could occur with only 4 consecutive base pairs (14%). With probes, 17% and 22% of the total sequence of Sign-B4-B0 (7/41 bp) and NK-toxB-B34-A0 (7/32 bp), respectively, could be used to form homoduplexes. This is not sufficient to create stable structures. In the same way, heteroduplexes involving a number of consecutive nucleotides lower than 25% of the shortest sequence size are very unlikely to form (Table 5). Consequently, all the structures able to be formed will be unstable and 18% is the greatest percentage met.

TABLE 5

| | KERLA-tcdB-2873 (length 28 bp) | | KENP-tcdB-3102 (length 28 bp) | | Sign-B4-B0 (length 41 bp) | | NK-toxB-B34-A0 (length 32 bp) | |
|---|---|---|---|---|---|---|---|---|
| | Consecutive nucleotide duplexes | Delta G | Consecutive nucleotide duplexes | Delta G | Consecutive nucleotide duplexes | Delta G | Consecutive nucleotide duplexes | Delta G |
| KERLA-tcdB-2873 | 6 | −10.46 | | | | | | |
| (length 28 bp) | 6 | −8.74 | | | | | | |
| | 4 | −7.05 | | | | | | |
| KENP-tcdB-3102 | 4 | −7.05 | 4 | −7.05 | | | | |
| (length 28 bp) | 5 | −5.34 | 4 | −3.40 | | | | |
| | 3 | −5.09 | 3 | −2.91 | | | | |
| Sign B4-B0 | 4 | −6.57 | 3 | −5.09 | 7 | −18.08 | | |
| (length 41 bp) | 4 | −5.37 | 3 | −5.09 | 4 | −9.75 | | |
| | 4 | −5.37 | 4 | −5.00 | 4 | −9.75 | | |
| NK-toxB-B34-A0 | 4 | −7.05 | 4 | −7.05 | 3 | −6.68 | 7 | −13.26 |
| (length 32 bp) | 4 | −5.24 | 4 | −4.50 | 3 | −6.68 | 4 | −7.05 |
| | 3 | −5.09 | 3 | −4.41 | 3 | −6.68 | 5 | −6.82 |

Figure 2A:
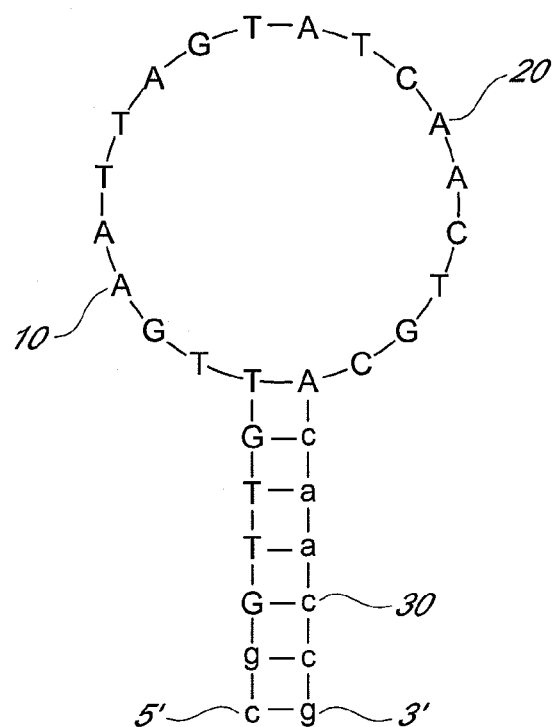
FIG. 2A is a schematic diagram showing the hairpin structure formed with the NK-toxB-B34-A0 target probe (SEQ ID NO:30).
Figure 2B:
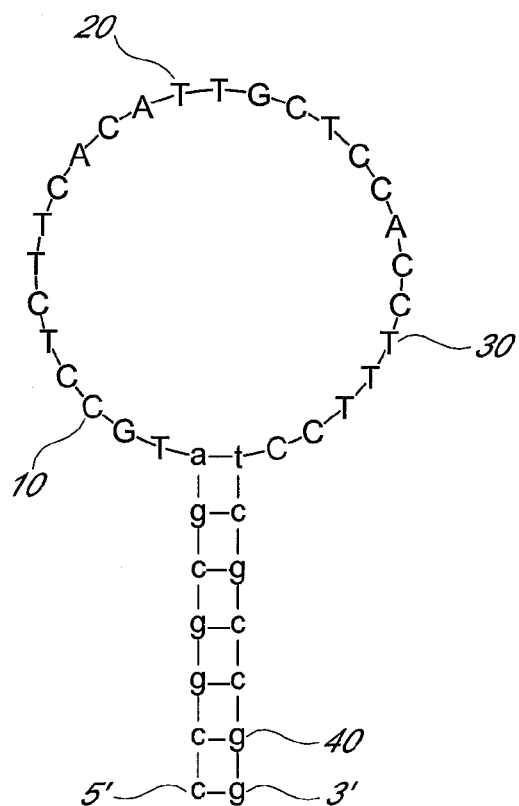
FIG. 2B is a schematic diagram showing the hairpin structure formed with the Sign-B4-B0 internal control probe (SEQ ID NO:31).

The NK-toxB-B34-A0 target probe and Sign-B4-B0 internal control probe molecule each has an oligonucleotide probe sequence flanked on each side by complementary sequences (arms), carrying a fluorophore at its 5' end and a fluorescence quencher at its 3' end. In a closed conformation, the arms form a stem and the probe sequence is located in a hairpin loop (FIGS. 2A and 2B). In this conformation the fluorescence is quenched. However, when hybridizing with the target DNA, the hairpin structure unfolds and allows fluorescence. For each probe, structure was determined at two temperatures using *The Bioinformatics Center at Rensselaer and Wadsworth tools* (DNA folding in applications section); this web server uses mfold (version3.1) by Zuker and Turner (Zuker, *Nucleic Acids Res.* 31 (13), 3406-15, 2003). First, the probe structure at the synthesis temperature and salt conditions was determined (10 mM Na$^+$ and 20° C. without Mg$^{2+}$) and then the structure at the annealing temperature and salt conditions of the PCR assay was determined (100 mM Na$^+$, 57° C. and 5.5 mM Mg$^{2+}$). Only one structure was obtained for target probe as well as for IC probe (synthesis conditions and PCR conditions (see FIGS. 2A and 2B)). No stable probe dimer was identified.

The ability of all primers and probes to form self dimers (homodimers) or duplexes with another primer or probes of the assay (heterodimers) was evaluated with the IDT Oli- In one embodiment, to ensure the required specificity, the assay primers do not generate any amplified product with sequences other than *C. difficile*. Thus, the potential hybridization of the primers with non-*C. difficile* sequences was tested. Sequences homologous to each assay primer were identified using BLAST searches (version 2.2.15) from the GenBank databases. The likelihood of amplifying non-target sequences was then evaluated according to the following criteria:

- the hybridization of each primer pair on different strands or the hybridization of one given primer at two sites on the same target
- the number of nucleotides complementary to the target sequence. Namely, the last 2 nucleotides of primers 3' end should hybridize to the target to allow primer extension.
- the length of the DNA fragment generated by the primer pair. Fragments above 3 kb are well outside rapid PCR and molecular beacon detection technology's limits.

Results of these searches are summarized in Table 6. For both primers, only Toxin B gene sequence from *C. difficile* strains showed 100% identity with primer sequences.

TABLE 6

| Primer name | Primer length (nucleotides) | Total identified | tcdB 100% identity | Source (n) |
|---|---|---|---|---|
| KERLA-tcdB-2873 | 28 | 103 | 6 | *Clostridium difficile* 630 complete genome (AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |
| KENP-tcdB-3102 | 28 | 50 | 6 | *Clostridium difficile* 630 complete genome (AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |

To ensure that probes hybridized only with *C. difficile* amplicons, and had the required sensitivity, the potential hybridization of the probes with non-*C. difficile* sequences was tested. Sequences homologous to each of the assay probes were identified using BLAST searches (version 2.2.15) of the GenBank databases. Results of these searches are summarized in Table 7. For the target probe, only the Toxin B gene sequence from *C. difficile* strains showed 100% identity with the probe sequence. For the internal control probe, only the *Drosophila melanogaster* sequence showed 100% identity with the probe sequence. The Internal control probe was designed from the *Drosophila melanogaster* sequence.

TABLE 7

| | | Number of Identified sequences | | |
|---|---|---|---|---|
| Probe name | Probe length (nucleotides) | Total identified | 100% homology with target[1] | Source (n) |
| NK-toxB-B34-A0 | 24 | 23 | 6 | *Clostridium difficile* 630 complete genome (AM180335.1)<br>*C. difficile* gene for toxin B (Z23277.1)<br>*C. difficile* cdu2, cdu1, tcdD, tcdB, tcdE, tcdA, tcdC, cdd1, cdd2, cdd3, and cdd4 genes (X92982.1)<br>*Clostridium difficile* toxB gene for toxin B (X53138.1)<br>*Clostridium difficile* (strain 8864) pathogenicity DNA locus (tcdD, tcdB, tcdE, tcdA and partial cdd1 and cdu1 genes) (AJ011301.1)<br>*Clostridium difficile* cytotoxin B (tcdB) gene, complete cds (AF217292.1) |
| Sign-B4-B0 | 27 | 77 | 14[2] | *Drosophila melanogaster* genomic scaffold 211000022280790<br>*Drosophila melanogaster* genomic scaffold 211000022280724<br>*Drosophila melanogaster* genomic scaffold 211000022280794<br>*Drosophila melanogaster* genomic scaffold 211000022280749<br>*Drosophila melanogaster* chromosome 3L, complete sequence |

TABLE 7-continued

| Probe name | Probe length (nucleotides) | Total identified | 100% homology with target[1] | Source (n) |
|---|---|---|---|---|
| | | | | *Drosophila melanogaster* chromosome 2R, complete sequence |
| | | | | *Drosophila melanogaster* genomic scaffold 211000022280741 |
| | | | | *Drosophila melanogaster* genomic scaffold 211000022280785 |
| | | | | *Drosophila melanogaster* genomic scaffold 211000022280616 |
| | | | | *Drosophila melanogaster* clone BACR11B22, complete sequence |
| | | | | *Drosophila simulans* w gene, retrotransposons ninja1, ninja2, ninja3, strain: w[mky] |
| | | | | *Drosophila simulans* w gene, retrotransposon ninja, strain: w[apl] |
| | | | | *Drosophila simulans* retrotransposon ninja DNA |
| | | | | *Drosophila melanogaster* retrotransposon aurora DNA |

[1]Toxin B gene for NK-toxB-B34-A0 or internal control signature sequence for Sign-B4-B0
[2]The Internal control was designed from *D. melanogaster* sequences Specificity and Sensitivity Twenty-two different *C. difficile* toxinotypes were tested with the probes shown in Table 4. Positive results were obtained for all toxinotypes, but not for any related species, *C. sordelli*, *C. difficile* A-/B-strain or non-toxigenic *C. difficile* strain. Thus, the probes are specific to toxigenic strains of *C. difficile*.

Real-time PCR was performed under standard conditions using *C. difficile* DNA obtained from liquid or soft human stool samples using the primers shown in Table 3. The real-time PCR assay was performed as described below.

Real-Time PCR Assay

Lyophilized reagents were reconstituted with 225 µl diluent to provide the following buffer used for the real-time PCR assay: 116 mM Tris-HCl, pH 8.3, 11.6 mM KCl, 3.48 mM $MgCl_2$, 5.8 mM $NH_2SO_4$, and subsequently divided into 25 µl aliquots. 0.5, 2.5, 5, 10 or 20 copies of *C. difficile* template DNA was added to each of 5 replicate reactions.

The PCR assay was run in a SMART CYCLER™ PCR machine under the following conditions: 60° C. for 6 sec, followed by 95° C. for 900 sec, followed by 45 cycles of 95° C. for 5 seconds, 63° C. for 10 sec and 72° C. for 20 sec. The sensitivity and specificity obtained were 96.6% and 97.4%, respectively.

What is claimed is:

1. A mixture for detecting the presence of a toxigenic strain of *C. difficile* in a biological sample, comprising:
at least one pair of primers capable of binding to a *C. difficile* toxin B (TcdB) gene and amplifying target nucleic acids from the biological sample to produce an amplified product(s), wherein each primer in said at least one pair of primers is up to 50 nucleotides in length, and wherein said at least one pair of primers comprises a primer comprising the sequence of SEQ ID NO: 16 and a primer comprising the sequence of SEQ ID NO: 19;
a DNA polymerase;
a plurality of dNTPs; and
an oligonucleotide probe comprising a target-specific sequence complementary to the sequence of the amplified product(s), wherein the oligonucleotide probe is up to 100 nucleotides in length and capable of forming a stem-and-loop structure, and wherein at least a portion of the sequence of the stem is not complementary to the sequence of the amplified product(s).

2. The mixture of claim 1, further comprising nucleic acids from the biological sample.

3. The mixture of claim 2, wherein the nucleic acids comprise *C. difficile* DNA.

4. The mixture of claim 1, wherein the biological sample is selected from the group consisting of stool, sputum, peripheral blood, plasma, serum, lymph nodes, respiratory tissue, and exudates.

5. The mixture of claim 1, wherein the biological sample is a stool sample.

6. The mixture of claim 1, wherein said oligonucleotide probe comprises a fluorophore at the 5' end, and a fluorescence quencher at the 3' end.

7. The mixture of claim 1, wherein the oligonucleotide probe comprises the sequence of SEQ ID NO: 30 or SEQ ID NO: 31.

8. The mixture of claim 1, wherein the oligonucleotide probe comprises the sequence of SEQ ID NO: 30.

9. The mixture of claim 1, wherein the DNA polymerase is Taq polymerase.

10. The mixture of claim 1, wherein said at least one pair of primers comprises a primer consisting of the sequence of SEQ ID NO: 16 and a primer consisting of the sequence of SEQ ID NO: 19.

11. The mixture of claim 1, further comprising a buffer.

12. The mixture of claim 1, further comprising $MgCl_2$.

13. The mixture of claim 1, wherein the oligonucleotide probe is 20 to 30 nucleotides in length.

* * * * *

UNITED STATES PATENT AND TRADEMARK OFFICE
CERTIFICATE OF CORRECTION

PATENT NO. : 9,863,007 B2
APPLICATION NO. : 14/752586
DATED : January 9, 2018
INVENTOR(S) : Nancy Paquette et al.

It is certified that error appears in the above-identified patent and that said Letters Patent is hereby corrected as shown below:

In the Drawings

Sheet 1 of 3 (FIG. 1) at Line 11 (approx.), Change "acitvity" to --activity--.

In the Specification

In Column 1 at Line 7, Before "of" delete "under 35 U.S.C. §121".

In Column 1 at Line 54, Change "pseudomenbranous" to --pseudomembranous--.

In Column 1 at Line 62, Change "tdcD," to --tcdD,--.

In Column 1 at Line 62, Change "19,6" to --19.6--.

In Column 2 at Line 8, Change "(Tens)" to --(Tcns)--.

In Column 2 at Line 11, Change "disagreggation" to --disaggregation--.

In Column 2 at Line 53, Change "no 16," to --no. 16,--.

In Column 3 at Line 57, Before "IX," insert --I-VII,--.

In Column 4 at Line 5 (approx.), Change "Toxin," to --Toxin--.

In Column 5 at Line 8, Change "NO:" to --NOS:--.

In Column 5 at Line 12 (approx.), Change "NO:" to --NOS:--.

In Column 6 at Line 16, Change "toxogenic" to --toxigenic--.

Signed and Sealed this
Fifth Day of June, 2018

Andrei Iancu
*Director of the United States Patent and Trademark Office*

In Column 9 at Line 46, Change "ELIS A," to --ELISA,--.

In Column 9 at Line 54, Change "www.perlinks.com." to --www.pcrlinks.com.--.

In Column 10 at Line 64, Change "Na+" to --$Na^+$--.

In Columns 11-12 at Line 61 (approx.) in TABLE 3, Change "NO: 30)" to --NO: 16)--.

In Columns 13-14 at Line 5 in TABLE 3, Change "NO: 31)" to --NO: 19)--.

In Column 14 at Line 19, After "80%" insert --.--.

In Columns 13-14 at Line 50 in TABLE 4, Change "NO: 32)" to --NO: 30)--.

In Columns 13-14 at Line 52 in TABLE 4, Change "NO: 33)" to --NO: 31)--.

In Column 16 at Line 56, Change "target" to --target.--.

In Column 19 at Line 32 (approx.), Change "sordelli," to --sordellii,--.